US010303258B2

(12) United States Patent
Todeschini

(10) Patent No.: US 10,303,258 B2
(45) Date of Patent: *May 28, 2019

(54) INDICIA-READING SYSTEMS HAVING AN INTERFACE WITH A USER'S NERVOUS SYSTEM

(71) Applicant: Hand Held Products, Inc., Fort Mill, SC (US)

(72) Inventor: Erik Todeschini, Camillus, NY (US)

(73) Assignee: HAND HELD PRODUCTS, INC., Fort Mill, SC (US)

( * ) Notice: Subject to any disclaimer, the term of this patent is extended or adjusted under 35 U.S.C. 154(b) by 24 days.

This patent is subject to a terminal disclaimer.

(21) Appl. No.: 15/357,044

(22) Filed: Nov. 21, 2016

(65) Prior Publication Data

US 2017/0139484 A1 May 18, 2017

Related U.S. Application Data

(63) Continuation of application No. 14/735,717, filed on Jun. 10, 2015, now Pat. No. 9,507,974.

(51) Int. Cl.
*G06F 3/01* (2006.01)
*G06K 7/016* (2006.01)
(Continued)

(52) U.S. Cl.
CPC ............ *G06F 3/017* (2013.01); *A61B 5/0476* (2013.01); *A61B 5/168* (2013.01); *A61B 5/18* (2013.01);
(Continued)

(58) Field of Classification Search
CPC ......... G06F 3/017; G06F 3/015; G06K 7/016; G06K 7/10891; B60W 40/09;
(Continued)

(56) References Cited

U.S. PATENT DOCUMENTS 4,766,299 A * 8/1988 Tierney .............. G06K 7/10891
235/462.21
5,191,197 A * 3/1993 Metlitsky ........... G06K 7/10564
235/462.44
(Continued)

FOREIGN PATENT DOCUMENTS

WO 2013163789 A1 11/2013
WO 2013173985 A1 11/2013
(Continued)

OTHER PUBLICATIONS

Extended European Search Report in related European Application No. 17187839.0 dated Nov. 23, 2017, pp. 1-5.
(Continued)

*Primary Examiner* — Daniel I Walsh
(74) *Attorney, Agent, or Firm* — Additon, Higgins & Pendleton, P.A.

(57) ABSTRACT

Indicia-reading systems that interface with a user's nervous system include a device with electrodes capable of detecting electromagnetic signals produced in the brain or skeletal muscles of a user. The systems also include a computer with a processor and memory. The computer is configured to monitor the electromagnetic signals that are detected by the electrodes. The computer is also configured to perform operations in response to certain monitored electromagnetic signals. The computer may be an indicia-reading device configured to acquire indicia information in response to certain detected electromagnetic signals. The computer may also be a vehicle-mounted computer configured to sound an alarm in response to certain detected electromagnetic signals.

19 Claims, 4 Drawing Sheets

(51) Int. Cl.
  *B60W 40/09* (2012.01)
  *A61B 5/00* (2006.01)
  *G06K 7/10* (2006.01)
  *A61B 5/0476* (2006.01)
  *A61B 5/16* (2006.01)
  *A61B 5/18* (2006.01)
  *B60W 40/08* (2012.01)

(52) U.S. Cl.
  CPC ........... *A61B 5/6814* (2013.01); *B60W 40/08* (2013.01); *B60W 40/09* (2013.01); *G06F 3/015* (2013.01); *G06K 7/016* (2013.01); *G06K 7/10891* (2013.01); *B60W 2040/0827* (2013.01); *B60W 2040/0872* (2013.01); *B60W 2540/22* (2013.01)

(58) Field of Classification Search
  CPC ......... B60W 40/08; B60W 2040/0872; B60W 2040/0827; A61B 5/0476; A61B 5/168; A61B 5/18
  See application file for complete search history.

(56) References Cited

U.S. PATENT DOCUMENTS

| | | | |
|---|---|---|---|
| 5,250,790 | A * | 10/1993 | Melitsky ............ G06K 7/10564 235/462.44 |
| 5,484,992 | A * | 1/1996 | Wilz ........................ G06K 7/10 235/462.08 |
| 6,234,393 | B1 * | 5/2001 | Paratore ............. G06K 7/10891 235/462.2 |
| 6,806,863 | B1 * | 10/2004 | Howard ................... G06F 3/014 341/22 |
| 6,832,725 | B2 | 12/2004 | Gardiner et al. |
| 7,128,266 | B2 | 10/2006 | Zhu et al. |
| 7,159,783 | B2 | 1/2007 | Walczyk et al. |
| 7,413,127 | B2 | 8/2008 | Ehrhart et al. |
| 7,726,575 | B2 | 6/2010 | Wang et al. |
| 8,294,969 | B2 | 10/2012 | Plesko |
| 8,317,105 | B2 | 11/2012 | Kotlarsky et al. |
| 8,322,622 | B2 | 12/2012 | Liu et al. |
| 8,366,005 | B2 | 2/2013 | Kotlarsky et al. |
| 8,371,505 | B1 * | 2/2013 | Zolotov ............. G06K 7/10722 235/462.24 |
| 8,371,507 | B2 | 2/2013 | Haggerty et al. |
| 8,376,233 | B2 | 2/2013 | Van Horn et al. |
| 8,381,979 | B2 | 2/2013 | Franz |
| 8,390,909 | B2 | 3/2013 | Plesko |
| 8,408,464 | B2 | 4/2013 | Zhu et al. |
| 8,408,468 | B2 | 4/2013 | Horn et al. |
| 8,408,469 | B2 | 4/2013 | Good |
| 8,424,768 | B2 | 4/2013 | Rueblinger et al. |
| 8,448,863 | B2 | 5/2013 | Xian et al. |
| 8,457,013 | B2 | 6/2013 | Essinger et al. |
| 8,459,557 | B2 | 6/2013 | Havens et al. |
| 8,469,272 | B2 | 6/2013 | Kearney |
| 8,474,712 | B2 | 7/2013 | Kearney et al. |
| 8,479,992 | B2 | 7/2013 | Kotlarsky et al. |
| 8,490,877 | B2 | 7/2013 | Kearney |
| 8,517,271 | B2 | 8/2013 | Kotlarsky et al. |
| 8,523,076 | B2 | 9/2013 | Good |
| 8,528,818 | B2 | 9/2013 | Ehrhart et al. |
| 8,544,737 | B2 | 10/2013 | Gomez et al. |
| 8,548,420 | B2 | 10/2013 | Grunow et al. |
| 8,550,335 | B2 | 10/2013 | Samek et al. |
| 8,550,354 | B2 | 10/2013 | Gannon et al. |
| 8,550,357 | B2 | 10/2013 | Kearney |
| 8,556,174 | B2 | 10/2013 | Kosecki et al. |
| 8,556,176 | B2 | 10/2013 | Van Horn et al. |
| 8,556,177 | B2 | 10/2013 | Hussey et al. |
| 8,559,767 | B2 | 10/2013 | Barber et al. |
| 8,561,895 | B2 | 10/2013 | Gomez et al. |
| 8,561,903 | B2 | 10/2013 | Sauerwein |
| 8,561,905 | B2 | 10/2013 | Edmonds et al. |
| 8,565,107 | B2 | 10/2013 | Pease et al. |
| 8,571,307 | B2 | 10/2013 | Li et al. |
| 8,579,200 | B2 | 11/2013 | Samek et al. |
| 8,583,924 | B2 | 11/2013 | Caballero et al. |
| 8,584,945 | B2 | 11/2013 | Wang et al. |
| 8,587,595 | B2 | 11/2013 | Wang |
| 8,587,697 | B2 | 11/2013 | Hussey et al. |
| 8,588,869 | B2 | 11/2013 | Sauerwein et al. |
| 8,590,789 | B2 | 11/2013 | Nahill et al. |
| 8,596,539 | B2 | 12/2013 | Havens et al. |
| 8,596,542 | B2 | 12/2013 | Havens et al. |
| 8,596,543 | B2 | 12/2013 | Havens et al. |
| 8,599,271 | B2 | 12/2013 | Havens et al. |
| 8,599,957 | B2 | 12/2013 | Peake et al. |
| 8,600,158 | B2 | 12/2013 | Li et al. |
| 8,600,167 | B2 | 12/2013 | Showering |
| 8,602,309 | B2 | 12/2013 | Longacre et al. |
| 8,608,053 | B2 | 12/2013 | Meier et al. |
| 8,608,071 | B2 | 12/2013 | Liu et al. |
| 8,611,309 | B2 | 12/2013 | Wang et al. |
| 8,615,487 | B2 | 12/2013 | Gomez et al. |
| 8,621,123 | B2 | 12/2013 | Caballero |
| 8,622,303 | B2 | 1/2014 | Meier et al. |
| 8,628,013 | B2 | 1/2014 | Ding |
| 8,628,015 | B2 | 1/2014 | Wang et al. |
| 8,628,016 | B2 | 1/2014 | Winegar |
| 8,629,926 | B2 | 1/2014 | Wang |
| 8,630,491 | B2 | 1/2014 | Longacre et al. |
| 8,635,309 | B2 | 1/2014 | Berthiaume et al. |
| 8,636,200 | B2 | 1/2014 | Kearney |
| 8,636,212 | B2 | 1/2014 | Nahill et al. |
| 8,636,215 | B2 | 1/2014 | Ding et al. |
| 8,636,224 | B2 | 1/2014 | Wang |
| 8,638,806 | B2 | 1/2014 | Wang et al. |
| 8,640,958 | B2 | 2/2014 | Lu et al. |
| 8,640,960 | B2 | 2/2014 | Wang et al. |
| 8,643,717 | B2 | 2/2014 | Li et al. |
| 8,646,692 | B2 | 2/2014 | Meier et al. |
| 8,646,694 | B2 | 2/2014 | Wang et al. |
| 8,657,200 | B2 | 2/2014 | Ren et al. |
| 8,659,397 | B2 | 2/2014 | Vargo et al. |
| 8,668,149 | B2 | 3/2014 | Good |
| 8,678,285 | B2 | 3/2014 | Kearney |
| 8,678,286 | B2 | 3/2014 | Smith et al. |
| 8,682,077 | B1 | 3/2014 | Longacre |
| D702,237 | S | 4/2014 | Oberpriller et al. |
| 8,687,282 | B2 | 4/2014 | Feng et al. |
| 8,692,927 | B2 | 4/2014 | Pease et al. |
| 8,695,880 | B2 | 4/2014 | Bremer et al. |
| 8,698,949 | B2 | 4/2014 | Grunow et al. |
| 8,702,000 | B2 | 4/2014 | Barber et al. |
| 8,717,494 | B2 | 5/2014 | Gannon |
| 8,720,783 | B2 | 5/2014 | Biss et al. |
| 8,723,804 | B2 | 5/2014 | Fletcher et al. |
| 8,723,904 | B2 | 5/2014 | Marty et al. |
| 8,727,223 | B2 | 5/2014 | Wang |
| 8,740,082 | B2 | 6/2014 | Wilz |
| 8,740,085 | B2 | 6/2014 | Furlong et al. |
| 8,746,563 | B2 | 6/2014 | Hennick et al. |
| 8,750,445 | B2 | 6/2014 | Peake et al. |
| 8,752,766 | B2 | 6/2014 | Xian et al. |
| 8,756,059 | B2 | 6/2014 | Braho et al. |
| 8,757,495 | B2 | 6/2014 | Qu et al. |
| 8,760,563 | B2 | 6/2014 | Koziol et al. |
| 8,763,909 | B2 | 7/2014 | Reed et al. |
| 8,777,108 | B2 | 7/2014 | Coyle |
| 8,777,109 | B2 | 7/2014 | Oberpriller et al. |
| 8,779,898 | B2 | 7/2014 | Havens et al. |
| 8,781,520 | B2 | 7/2014 | Payne et al. |
| 8,783,573 | B2 | 7/2014 | Havens et al. |
| 8,789,757 | B2 | 7/2014 | Barten |
| 8,789,758 | B2 | 7/2014 | Hawley et al. |
| 8,789,759 | B2 | 7/2014 | Xian et al. |
| 8,794,520 | B2 | 8/2014 | Wang et al. |
| 8,794,522 | B2 | 8/2014 | Ehrhart |
| 8,794,525 | B2 | 8/2014 | Amundsen et al. |
| 8,794,526 | B2 | 8/2014 | Wang et al. |
| 8,798,367 | B2 | 8/2014 | Ellis |
| 8,807,431 | B2 | 8/2014 | Wang et al. |

(56) References Cited

U.S. PATENT DOCUMENTS

| | | |
|---|---|---|
| 8,807,432 B2 | 8/2014 | Van Horn et al. |
| 8,820,630 B2 | 9/2014 | Qu et al. |
| 8,822,848 B2 | 9/2014 | Meagher |
| 8,824,692 B2 | 9/2014 | Sheerin et al. |
| 8,824,696 B2 | 9/2014 | Braho |
| 8,842,849 B2 | 9/2014 | Wahl et al. |
| 8,844,822 B2 | 9/2014 | Kotlarsky et al. |
| 8,844,823 B2 | 9/2014 | Fritz et al. |
| 8,849,019 B2 | 9/2014 | Li et al. |
| D716,285 S | 10/2014 | Chaney et al. |
| 8,851,383 B2 | 10/2014 | Yeakley et al. |
| 8,854,633 B2 | 10/2014 | Laffargue |
| 8,866,963 B2 | 10/2014 | Grunow et al. |
| 8,868,421 B2 | 10/2014 | Braho et al. |
| 8,868,519 B2 | 10/2014 | Maloy et al. |
| 8,868,802 B2 | 10/2014 | Barten |
| 8,868,803 B2 | 10/2014 | Caballero |
| 8,870,074 B1 | 10/2014 | Gannon |
| 8,879,639 B2 | 11/2014 | Sauerwein |
| 8,880,426 B2 | 11/2014 | Smith |
| 8,881,983 B2 | 11/2014 | Havens et al. |
| 8,881,987 B2 | 11/2014 | Wang |
| 8,903,172 B2 | 12/2014 | Smith |
| 8,908,995 B2 | 12/2014 | Benos et al. |
| 8,910,870 B2 | 12/2014 | Li et al. |
| 8,910,875 B2 | 12/2014 | Ren et al. |
| 8,914,290 B2 | 12/2014 | Hendrickson et al. |
| 8,914,788 B2 | 12/2014 | Pettinelli et al. |
| 8,915,439 B2 | 12/2014 | Feng et al. |
| 8,915,444 B2 | 12/2014 | Havens et al. |
| 8,916,789 B2 | 12/2014 | Woodburn |
| 8,918,250 B2 | 12/2014 | Hollifield |
| 8,918,564 B2 | 12/2014 | Caballero |
| 8,925,818 B2 | 1/2015 | Kosecki et al. |
| 8,939,374 B2 | 1/2015 | Jovanovski et al. |
| 8,942,480 B2 | 1/2015 | Ellis |
| 8,944,313 B2 | 2/2015 | Williams et al. |
| 8,944,327 B2 | 2/2015 | Meier et al. |
| 8,944,332 B2 | 2/2015 | Harding et al. |
| 8,950,678 B2 | 2/2015 | Germaine et al. |
| D723,560 S | 3/2015 | Zhou et al. |
| 8,967,468 B2 | 3/2015 | Gomez et al. |
| 8,971,346 B2 | 3/2015 | Sevier |
| 8,976,030 B2 | 3/2015 | Cunningham et al. |
| 8,976,368 B2 | 3/2015 | Akel et al. |
| 8,978,981 B2 | 3/2015 | Guan |
| 8,978,983 B2 | 3/2015 | Bremer et al. |
| 8,978,984 B2 | 3/2015 | Hennick et al. |
| 8,985,456 B2 | 3/2015 | Zhu et al. |
| 8,985,457 B2 | 3/2015 | Soule et al. |
| 8,985,459 B2 | 3/2015 | Keamey et al. |
| 8,985,461 B2 | 3/2015 | Gelay et al. |
| 8,988,578 B2 | 3/2015 | Showering |
| 8,988,590 B2 | 3/2015 | Gillet et al. |
| 8,991,704 B2 | 3/2015 | Hopper et al. |
| 8,996,194 B2 | 3/2015 | Davis et al. |
| 8,996,384 B2 | 3/2015 | Funyak et al. |
| 8,998,091 B2 | 4/2015 | Edmonds et al. |
| 9,002,641 B2 | 4/2015 | Showering |
| 9,007,368 B2 | 4/2015 | Laffargue et al. |
| 9,010,641 B2 | 4/2015 | Qu et al. |
| 9,015,513 B2 | 4/2015 | Murawski et al. |
| 9,016,576 B2 | 4/2015 | Brady et al. |
| D730,357 S | 5/2015 | Fitch et al. |
| 9,022,288 B2 | 5/2015 | Nahill et al. |
| 9,030,964 B2 | 5/2015 | Essinger et al. |
| 9,033,240 B2 | 5/2015 | Smith et al. |
| 9,033,242 B2 | 5/2015 | Gillet et al. |
| 9,036,054 B2 | 5/2015 | Koziol et al. |
| 9,037,344 B2 | 5/2015 | Chamberlin |
| 9,038,911 B2 | 5/2015 | Xian et al. |
| 9,038,915 B2 | 5/2015 | Smith |
| D730,901 S | 6/2015 | Oberpriller et al. |
| D730,902 S | 6/2015 | Fitch et al. |
| D733,112 S | 6/2015 | Chaney et al. |
| 9,047,098 B2 | 6/2015 | Barten |
| 9,047,359 B2 | 6/2015 | Caballero et al. |
| 9,047,420 B2 | 6/2015 | Caballero |
| 9,047,525 B2 | 6/2015 | Barber |
| 9,047,531 B2 | 6/2015 | Showering et al. |
| 9,049,640 B2 | 6/2015 | Wang et al. |
| 9,053,055 B2 | 6/2015 | Caballero |
| 9,053,378 B1 | 6/2015 | Hou et al. |
| 9,053,380 B2 | 6/2015 | Xian et al. |
| 9,057,641 B2 | 6/2015 | Amundsen et al. |
| 9,058,526 B2 | 6/2015 | Powilleit |
| 9,064,165 B2 | 6/2015 | Havens et al. |
| 9,064,167 B2 | 6/2015 | Xian et al. |
| 9,064,168 B2 | 6/2015 | Todeschini et al. |
| 9,064,254 B2 | 6/2015 | Todeschini et al. |
| 9,066,032 B2 | 6/2015 | Wang |
| 9,070,032 B2 | 6/2015 | Corcoran |
| D734,339 S | 7/2015 | Zhou et al. |
| D734,751 S | 7/2015 | Oberpriller et al. |
| 9,082,023 B2 | 7/2015 | Feng et al. |
| 9,224,022 B2 | 12/2015 | Ackley et al. |
| 9,224,027 B2 | 12/2015 | Van Horn et al. |
| D747,321 S | 1/2016 | London et al. |
| 9,229,526 B1 * | 1/2016 | Neglur .................. G06F 15/76 |
| 9,230,140 B1 | 1/2016 | Ackley |
| 9,443,123 B2 | 1/2016 | Hejl |
| 9,250,712 B1 | 2/2016 | Todeschini |
| 9,258,033 B2 | 2/2016 | Showering |
| 9,262,633 B1 | 2/2016 | Todeschini et al. |
| 9,310,609 B2 | 4/2016 | Rueblinger et al. |
| D757,009 S | 5/2016 | Oberpriller et al. |
| 9,342,724 B2 | 5/2016 | McCloskey |
| 9,375,945 B1 | 6/2016 | Bowles |
| D760,719 S | 7/2016 | Zhou et al. |
| 9,390,596 B1 | 7/2016 | Todeschini |
| D762,604 S | 8/2016 | Fitch et al. |
| D762,647 S | 8/2016 | Fitch et al. |
| 9,412,242 B2 | 8/2016 | Van Horn et al. |
| D766,244 S | 9/2016 | Zhou et al. |
| 9,443,222 B2 | 9/2016 | Singel et al. |
| 9,478,113 B2 | 10/2016 | Xie et al. |
| 9,507,974 B1 * | 11/2016 | Todeschini ............. G06K 7/016 |
| 2004/0245341 A1 * | 12/2004 | Shimoda ............ G06K 7/10881 |
| | | 235/462.46 |
| 2004/0249510 A1 * | 12/2004 | Hanson .................. G06N 3/008 |
| | | 700/245 |
| 2005/0228515 A1 * | 10/2005 | Musallam ................ A61F 2/68 |
| | | 700/83 |
| 2006/0231628 A1 * | 10/2006 | Wei .................... G06K 7/10881 |
| | | 235/462.3 |
| 2006/0258408 A1 | 11/2006 | Tuomela et al. |
| 2007/0010756 A1 | 1/2007 | Viertio-Oja |
| 2007/0063048 A1 | 3/2007 | Havens et al. |
| 2007/0124027 A1 | 5/2007 | Betziza et al. |
| 2008/0212849 A1 * | 9/2008 | Gao .................... G06K 9/00255 |
| | | 382/118 |
| 2008/0228365 A1 | 9/2008 | White et al. |
| 2008/0312551 A1 * | 12/2008 | Fadem ............... A61B 5/04001 |
| | | 600/554 |
| 2009/0040054 A1 | 2/2009 | Wang et al. |
| 2009/0134221 A1 | 5/2009 | Zhu et al. |
| 2009/0227965 A1 | 9/2009 | Wijesiriwardana |
| 2009/0327171 A1 * | 12/2009 | Tan ........................ G06F 3/015 |
| | | 706/12 |
| 2010/0094502 A1 | 4/2010 | Ito |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2010/0258618 A1 * | 10/2010 | Philbrick ............... G06K 19/06 |
| | | 235/375 |
| 2011/0169999 A1 | 7/2011 | Grunow et al. |
| 2011/0187640 A1 | 8/2011 | Jacobsen et al. |
| 2011/0202554 A1 | 8/2011 | Powilleit et al. |
| 2011/0213511 A1 | 9/2011 | Visconti et al. |
| 2012/0046531 A1 * | 2/2012 | Hua ...................... A61B 5/6865 |
| | | 600/317 |
| 2012/0111946 A1 | 5/2012 | Golant |

(56) References Cited

U.S. PATENT DOCUMENTS

| | | |
|---|---|---|
| 2012/0168512 A1 | 7/2012 | Kotlarsky et al. |
| 2012/0193423 A1 | 8/2012 | Samek |
| 2012/0203647 A1 | 8/2012 | Smith |
| 2012/0223141 A1 | 9/2012 | Good et al. |
| 2012/0224040 A1* | 9/2012 | Wang ............... G06K 7/1091 348/77 |
| 2013/0043312 A1 | 2/2013 | Van Horn |
| 2013/0075168 A1 | 3/2013 | Amundsen et al. |
| 2013/0130799 A1 | 5/2013 | Van Hulle et al. |
| 2013/0175341 A1 | 7/2013 | Kearney et al. |
| 2013/0175343 A1 | 7/2013 | Good |
| 2013/0194200 A1* | 8/2013 | Zanone ............... G06F 3/0418 345/173 |
| 2013/0204153 A1 | 8/2013 | Buzhardt |
| 2013/0226408 A1 | 8/2013 | Fung et al. |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0287258 A1 | 10/2013 | Kearney |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0296731 A1 | 11/2013 | Kidmose et al. |
| 2013/0306728 A1 | 11/2013 | Thuries et al. |
| 2013/0306731 A1 | 11/2013 | Pedraro |
| 2013/0307964 A1 | 11/2013 | Bremer et al. |
| 2013/0308625 A1 | 11/2013 | Park et al. |
| 2013/0313324 A1 | 11/2013 | Koziol et al. |
| 2013/0313325 A1 | 11/2013 | Wilz et al. |
| 2013/0342717 A1 | 12/2013 | Havens et al. |
| 2014/0001267 A1 | 1/2014 | Giordano et al. |
| 2014/0002806 A1* | 1/2014 | Buchel ............... G01S 7/48 356/4.01 |
| 2014/0002828 A1 | 1/2014 | Laffargue et al. |
| 2014/0008439 A1 | 1/2014 | Wang |
| 2014/0025584 A1 | 1/2014 | Liu et al. |
| 2014/0100813 A1 | 1/2014 | Showering |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0050354 A1* | 2/2014 | Heim ............... G06K 9/00335 382/103 |
| 2014/0059066 A1* | 2/2014 | Koloskov ............... G06F 17/30017 707/758 |
| 2014/0061306 A1 | 3/2014 | Wu et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |
| 2014/0071840 A1 | 3/2014 | Venancio |
| 2014/0074746 A1 | 3/2014 | Wang |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |
| 2014/0098792 A1 | 4/2014 | Wang et al. |
| 2014/0100774 A1 | 4/2014 | Showering |
| 2014/0103115 A1 | 4/2014 | Meier et al. |
| 2014/0104413 A1 | 4/2014 | McCloskey et al. |
| 2014/0104414 A1 | 4/2014 | McCloskey et al. |
| 2014/0104416 A1 | 4/2014 | Giordano et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |
| 2014/0131441 A1 | 5/2014 | Nahill et al. |
| 2014/0131443 A1 | 5/2014 | Smith |
| 2014/0131444 A1 | 5/2014 | Wang |
| 2014/0131445 A1 | 5/2014 | Ding et al. |
| 2014/0131448 A1 | 5/2014 | Xian et al. |
| 2014/0133379 A1 | 5/2014 | Wang et al. |
| 2014/0136208 A1 | 5/2014 | Maltseff et al. |
| 2014/0140585 A1 | 5/2014 | Wang |
| 2014/0151453 A1 | 6/2014 | Meier et al. |
| 2014/0152882 A1 | 6/2014 | Samek et al. |
| 2014/0158770 A1 | 6/2014 | Sevier et al. |
| 2014/0159869 A1 | 6/2014 | Zumsteg et al. |
| 2014/0166755 A1 | 6/2014 | Liu et al. |
| 2014/0166757 A1 | 6/2014 | Smith |
| 2014/0166759 A1 | 6/2014 | Liu et al. |
| 2014/0168787 A1 | 6/2014 | Wang et al. |
| 2014/0175165 A1 | 6/2014 | Havens et al. |
| 2014/0175172 A1 | 6/2014 | Jovanovski et al. |
| 2014/0191644 A1 | 7/2014 | Chaney |
| 2014/0191913 A1 | 7/2014 | Ge et al. |
| 2014/0197238 A1 | 7/2014 | Lui et al. |
| 2014/0197239 A1 | 7/2014 | Havens et al. |
| 2014/0197304 A1 | 7/2014 | Feng et al. |
| 2014/0203087 A1 | 7/2014 | Smith et al. |
| 2014/0204268 A1 | 7/2014 | Grunow et al. |
| 2014/0206323 A1 | 7/2014 | Scorcioni |
| 2014/0214631 A1 | 7/2014 | Hansen |
| 2014/0216174 A1* | 8/2014 | Aberg ............... G06F 3/041 73/862.628 |
| 2014/0217166 A1 | 8/2014 | Berthiaume et al. |
| 2014/0217180 A1 | 8/2014 | Liu |
| 2014/0231500 A1 | 8/2014 | Ehrhart et al. |
| 2014/0232930 A1 | 8/2014 | Anderson |
| 2014/0247315 A1 | 9/2014 | Marty et al. |
| 2014/0263493 A1 | 9/2014 | Amurgis et al. |
| 2014/0263645 A1 | 9/2014 | Smith et al. |
| 2014/0267142 A1* | 9/2014 | MacDougall ............... G06F 3/017 345/174 |
| 2014/0270196 A1 | 9/2014 | Braho et al. |
| 2014/0270229 A1 | 9/2014 | Braho |
| 2014/0278387 A1 | 9/2014 | DiGregorio |
| 2014/0282210 A1 | 9/2014 | Bianconi |
| 2014/0284384 A1 | 9/2014 | Lu et al. |
| 2014/0285404 A1* | 9/2014 | Takano ............... G06F 3/005 345/8 |
| 2014/0288933 A1 | 9/2014 | Braho et al. |
| 2014/0297058 A1 | 10/2014 | Barker et al. |
| 2014/0299665 A1 | 10/2014 | Barber et al. |
| 2014/0312121 A1 | 10/2014 | Lu et al. |
| 2014/0319220 A1 | 10/2014 | Coyle |
| 2014/0319221 A1 | 10/2014 | Oberpriller et al. |
| 2014/0326787 A1 | 11/2014 | Barten |
| 2014/0332590 A1 | 11/2014 | Wang et al. |
| 2014/0334083 A1 | 11/2014 | Bailey |
| 2014/0344943 A1 | 11/2014 | Todeschini et al. |
| 2014/0346233 A1 | 11/2014 | Liu et al. |
| 2014/0351317 A1 | 11/2014 | Smith et al. |
| 2014/0353373 A1 | 12/2014 | Van Horn et al. |
| 2014/0361073 A1 | 12/2014 | Qu et al. |
| 2014/0361082 A1 | 12/2014 | Xian et al. |
| 2014/0362184 A1 | 12/2014 | Jovanovski et al. |
| 2014/0363015 A1 | 12/2014 | Braho |
| 2014/0369511 A1 | 12/2014 | Sheerin et al. |
| 2014/0374483 A1 | 12/2014 | Lu |
| 2014/0374485 A1 | 12/2014 | Xian et al. |
| 2015/0001301 A1 | 1/2015 | Ouyang |
| 2015/0001304 A1 | 1/2015 | Todeschini |
| 2015/0003673 A1 | 1/2015 | Fletcher |
| 2015/0009338 A1 | 1/2015 | Laffargue et al. |
| 2015/0009610 A1 | 1/2015 | London et al. |
| 2015/0014416 A1 | 1/2015 | Kotlarsky et al. |
| 2015/0021397 A1 | 1/2015 | Rueblinger et al. |
| 2015/0028102 A1 | 1/2015 | Ren et al. |

(56) References Cited

U.S. PATENT DOCUMENTS

| | | |
|---|---|---|
| 2015/0028103 A1 | 1/2015 | Jiang |
| 2015/0028104 A1 | 1/2015 | Ma et al. |
| 2015/0029002 A1 | 1/2015 | Yeakley et al. |
| 2015/0032709 A1 | 1/2015 | Maloy et al. |
| 2015/0038231 A1* | 2/2015 | Mahlmeister ............ A63F 13/06 463/37 |
| 2015/0039309 A1 | 2/2015 | Braho et al. |
| 2015/0040378 A1 | 2/2015 | Saber et al. |
| 2015/0048168 A1 | 2/2015 | Fritz et al. |
| 2015/0049347 A1 | 2/2015 | Laffargue et al. |
| 2015/0051992 A1 | 2/2015 | Smith |
| 2015/0053766 A1 | 2/2015 | Havens et al. |
| 2015/0053768 A1 | 2/2015 | Wang et al. |
| 2015/0053769 A1 | 2/2015 | Thuries et al. |
| 2015/0062366 A1 | 3/2015 | Liu et al. |
| 2015/0063215 A1 | 3/2015 | Wang |
| 2015/0063676 A1 | 3/2015 | Lloyd et al. |
| 2015/0069130 A1 | 3/2015 | Gannon |
| 2015/0071819 A1 | 3/2015 | Todeschini |
| 2015/0083800 A1 | 3/2015 | Li et al. |
| 2015/0086114 A1 | 3/2015 | Todeschini |
| 2015/0088522 A1 | 3/2015 | Hendrickson et al. |
| 2015/0096872 A1 | 4/2015 | Woodburn |
| 2015/0099557 A1 | 4/2015 | Pettinelli et al. |
| 2015/0100196 A1 | 4/2015 | Hollifield |
| 2015/0102109 A1 | 4/2015 | Huck |
| 2015/0102562 A1* | 4/2015 | Cooley .................... A63F 1/02 273/293 |
| 2015/0109577 A1* | 4/2015 | Haddadi .................. A61B 3/11 351/204 |
| 2015/0115035 A1 | 4/2015 | Meier et al. |
| 2015/0123890 A1* | 5/2015 | Kapur .................. G06F 3/0304 345/156 |
| 2015/0127791 A1 | 5/2015 | Kosecki et al. |
| 2015/0128116 A1 | 5/2015 | Chen et al. |
| 2015/0129659 A1 | 5/2015 | Feng et al. |
| 2015/0133047 A1 | 5/2015 | Smith et al. |
| 2015/0134470 A1 | 5/2015 | Hejl et al. |
| 2015/0136851 A1 | 5/2015 | Harding et al. |
| 2015/0136854 A1 | 5/2015 | Lu et al. |
| 2015/0141529 A1 | 5/2015 | Hargrove |
| 2015/0142492 A1 | 5/2015 | Kumar |
| 2015/0144692 A1 | 5/2015 | Hejl |
| 2015/0144698 A1 | 5/2015 | Teng et al. |
| 2015/0144701 A1 | 5/2015 | Xian et al. |
| 2015/0145805 A1* | 5/2015 | Liu ............................ G06F 3/01 345/174 |
| 2015/0149946 A1 | 5/2015 | Benos et al. |
| 2015/0161429 A1 | 6/2015 | Xian |
| 2015/0169925 A1 | 6/2015 | Chang et al. |
| 2015/0169929 A1 | 6/2015 | Williams et al. |
| 2015/0186703 A1 | 7/2015 | Chen et al. |
| 2015/0193644 A1 | 7/2015 | Kearney et al. |
| 2015/0193645 A1 | 7/2015 | Colavito et al. |
| 2015/0199957 A1 | 7/2015 | Funyak et al. |
| 2015/0204671 A1 | 7/2015 | Showering |
| 2015/0210199 A1 | 7/2015 | Payne |
| 2015/0212585 A1* | 7/2015 | Latta ....................... G06F 3/005 345/158 |
| 2015/0220753 A1 | 8/2015 | Zhu et al. |
| 2015/0254485 A1 | 9/2015 | Feng et al. |
| 2015/0257673 A1 | 9/2015 | Lawrence et al. |
| 2015/0272465 A1 | 10/2015 | Ishii |
| 2015/0282760 A1 | 10/2015 | Badower et al. |
| 2015/0286285 A1* | 10/2015 | Pantelopoulos ..... A61B 5/6802 345/156 |
| 2015/0313496 A1 | 11/2015 | Connor |
| 2015/0313497 A1 | 11/2015 | Chang et al. |
| 2015/0313539 A1* | 11/2015 | Connor ................ A61B 5/7285 600/544 |
| 2015/0327012 A1 | 11/2015 | Bian et al. |
| 2015/0363082 A1* | 12/2015 | Zhao .................. G06F 3/04883 715/800 |
| 2015/0374255 A1 | 12/2015 | Vasapollo |
| 2016/0014251 A1 | 1/2016 | Hejl |
| 2016/0040982 A1 | 2/2016 | Li et al. |
| 2016/0042241 A1 | 2/2016 | Todeschini |
| 2016/0057230 A1 | 2/2016 | Todeschini et al. |
| 2016/0070439 A1* | 3/2016 | Bostick ............... G06F 3/04842 715/728 |
| 2016/0103487 A1* | 4/2016 | Crawford ................ G06F 3/015 600/544 |
| 2016/0109219 A1 | 4/2016 | Ackley et al. |
| 2016/0109220 A1 | 4/2016 | Laffargue |
| 2016/0109224 A1 | 4/2016 | Thuries et al. |
| 2016/0112631 A1 | 4/2016 | Ackley et al. |
| 2016/0112643 A1 | 4/2016 | Laffargue et al. |
| 2016/0124516 A1 | 5/2016 | Schoon et al. |
| 2016/0125217 A1 | 5/2016 | Todeschini |
| 2016/0125342 A1 | 5/2016 | Miller et al. |
| 2016/0132707 A1 | 5/2016 | Lindbo et al. |
| 2016/0133253 A1 | 5/2016 | Braho et al. |
| 2016/0171720 A1 | 6/2016 | Todeschini |
| 2016/0171772 A1* | 6/2016 | Ryznar ................. G02B 27/017 345/633 |
| 2016/0178479 A1 | 6/2016 | Goldsmith |
| 2016/0180678 A1 | 6/2016 | Ackley et al. |
| 2016/0188944 A1 | 6/2016 | Wilz et al. |
| 2016/0189087 A1 | 6/2016 | Morton et al. |
| 2016/0125873 A1 | 7/2016 | Braho et al. |
| 2016/0217621 A1* | 7/2016 | Raghoebardajal .... G06T 19/006 |
| 2016/0227912 A1 | 8/2016 | Oberpriller et al. |
| 2016/0232891 A1 | 8/2016 | Pecorari |
| 2016/0275483 A1* | 9/2016 | Zhou .................. G06Q 20/3278 |
| 2016/0292477 A1 | 10/2016 | Bidwell |
| 2016/0294779 A1 | 10/2016 | Yeakley et al. |
| 2016/0306769 A1 | 10/2016 | Kohtz et al. |
| 2016/0314276 A1 | 10/2016 | Sewell et al. |
| 2016/0314294 A1 | 10/2016 | Kubler et al. |
| 2016/0321742 A1* | 11/2016 | Phillips .................. G06Q 20/10 |
| 2017/0139484 A1* | 5/2017 | Todeschini .............. G06F 3/017 |

FOREIGN PATENT DOCUMENTS

| | | |
|---|---|---|
| WO | 2014019130 A1 | 2/2014 |
| WO | 2014110495 A1 | 7/2014 |

OTHER PUBLICATIONS

U.S. Appl. No. 14/715,916 for Evaluating Image Values filed May 19, 2015 (Ackley); 60 pages.

U.S. Appl. No. 29/525,068 for Tablet Computer With Removable Scanning Device filed Apr. 27, 2015 (Schulte et al.); 19 pages.

U.S. Appl. No. 29/468,118 for an Electronic Device Case, filed Sep. 26, 2013 (Oberpriller et al.); 44 pages.

U.S. Appl. No. 29/530,600 for Cyclone filed Jun. 18, 2015 (Vargo et al); 16 pages.

U.S. Appl. No. 14/707,123 for Application Independent DEX/UCS Interface filed May 8, 2015 (Pape); 47 pages.

U.S. Appl. No. 14/283,282 for Terminal Having Illumination and Focus Control filed May 21, 2014 (Lie et al.); 31 pages; now abandoned.

U.S. Appl. No. 14/705,407 for Method and System to Protect Software-Based Network-Connected Devices From Advanced Persistent Threat filed May 6, 2015 (Hussey et al.); 42 pages.

U.S. Appl. No. 14/704,050 for Intermediate Linear Positioning filed May 5, 2015 (Charpentier et al.); 60 pages.

U.S. Appl. No. 14/705,012 for Hands-Free Human Machine Interface Responsive to a Driver of a Vehicle filed May 6, 2015 (Fitch et al.); 44 pages.

U.S. Appl. No. 14/715,672 for Augmented Reality Enabled Hazard Display filed May 19, 2015 (Venkatesha et al.); 35 pages.

U.S. Appl. No. 14/735,717 for Indicia-Reading Systems Having an Interface With a User's Nervous System filed Jun. 10, 2015 (Todeschini); 39 pages.

U.S. Appl. No. 14/702,110 for System and Method for Regulating Barcode Data Injection Into a Running Application on a Smart Device filed May 1, 2015 (Todeschini et al.); 38 pages.

(56) References Cited

OTHER PUBLICATIONS

U.S. Appl. No. 14/747,197 for Optical Pattern Projector filed Jun. 23, 2015 (Thuries et al.); 33 pages.
U.S. Appl. No. 14/702,979 for Tracking Battery Conditions filed May 4, 2015 (Young et al.); 70 pages.
U.S. Appl. No. 29/529,441 for Indicia Reading Device filed Jun. 8, 2015 (Zhou et al.); 14 pages.
U.S. Appl. No. 14/747,490 for Dual-Projector Three-Dimensional Scanner filed Jun. 23, 2015 (Jovanovski et al.); 40 pages.
U.S. Appl. No. 14/740,320 for Tactile Switch for a Mobile Electronic Device filed Jun. 16, 2015 (Bamdringa); 38 pages.
U.S. Appl. No. 14/740,373 for Calibrating a Volume Dimensioner filed Jun. 16, 2015 (Ackley et al.); 63 pages.
Wikipedia, "Evoked potential" downloaded from: https://en.wikipedia.org/wiki/Evoked_potential, Sep. 17, 2015, pp. 1-9.
U.S. Appl. No. 13/367,978, filed Feb. 7, 2012, (Feng et al.); now abandoned.
U.S. Appl. No. 14/277,337 for Multipurpose Optical Reader, filed May 14, 2014 (Jovanovski et al.); 59 pages; now abandoned.
U.S. Appl. No. 14/446,391 for Multifunction Point of Sale Apparatus With Optical Signature Capture filed Jul. 30, 2014 (Good et al.); 37 pages; now abandoned.
U.S. Appl. No. 29/516,892 for Table Computer filed Feb. 6, 2015 (Bidwell et al.); 13 pages.
U.S. Appl. No. 29/523,098 for Handle for a Tablet Computer filed Apr. 7, 2015 (Bidwell et al.); 17 pages.
U.S. Appl. No. 29/528,890 for Mobile Computer Housing filed Jun. 2, 2015 (Fitch et al.); 61 pages.
U.S. Appl. No. 29/526,918 for Charging Base filed May 14, 2015 (Fitch et al.); 10 pages.

* cited by examiner

INDICIA-READING SYSTEMS HAVING AN INTERFACE WITH A USER'S NERVOUS SYSTEM

CROSS-REFERENCE TO RELATED APPLICATION

The present application claims the benefit of U.S. patent application Ser. No. 14/735,717 for Indicia-Reading Systems Having an Interface with a User's Nervous System filed Jun. 10, 2015, now U.S. Pat. No. 9,507,974. Each of the foregoing patent application and patent is hereby incorporated by reference in its entirety.

FIELD OF THE INVENTION

The present invention relates to the field of indicia-reading systems and, more specifically, to indicia-reading systems that interface with a user's nervous system.

BACKGROUND

Indicia readers, such as barcode scanners, are typically configured to acquire information from indicia and then decode that information for use in data systems. Traditional indicia-reading systems embrace various kinds of devices used to read indicia, including handheld barcode scanners.

Handheld indicia-reading devices, such as handheld barcode scanners and mobile computers, are currently used in numerous environments for various applications (e.g., warehouses, delivery vehicles, hospitals, etc.). In this regard, a large percentage of retailers, notably grocery stores and general consumer merchandisers, currently rely on barcode technology to improve the efficiency and reliability of the checkout process. Traditionally, a user interacts with a handheld indicia-reading device via a trigger or a touchscreen display.

More recently, wearable computing devices (e.g., GOOGLE GLASS™ from Google, Inc.) have been developed. Wearable computing devices may be used in indicia-reading systems. As these types of devices become more common, the options through which users can interface with these devices and systems will change and expand as the demand for hands-free interface grows stronger.

Current hands-free interface options for computing systems include gesture optical recognition (i.e., mathematical interpretation of human motion by a computing device). Gesture recognition can originate from any bodily motion or state, but commonly originates from the hands. Gesture interface provides a useful building block for a hands-free interface, but does not offer a completely hands-free experience as it is actually more of a touch-free interface that still requires free hands for gesturing.

A technology that does offer the possibility of a completely hands-free and touch-free interface is the brain-computer interface. For example, electroencephalography (EEG) can be used to detect electrical activity in the brain. Traditional EEG testing in a medical or laboratory environment involves flat metal discs (electrodes) attached directly to the scalp to measure the electrical activity of the brain (i.e., to measure brain waves). Traditional EEG testing equipment is inadequate for more mainstream applications, however, because it involves equipment that requires shaving the head, affixing gelled electrodes to the scalp, etc.

Recent advances in EEG, however, open the ability to read electrical signals produced by the brain to more mainstream applications. For instance, companies such as Emotiv Systems, an Australian electronics company, have brought EEG devices to market that do not require shaving a user's head or gels of any kind to measure the electrical activity of the brain. One such device is the EMOTIV INSIGHT™ from Emotiv Systems.

Another technology that opens the possibility to facilitate a hands-free or touch-free interface without the requirement of optical recognition of gestures is electromyography (EMG). EMG is a technique for evaluating and recording the electrical activity produced by skeletal muscles. EMG is performed using an instrument called an electromyograph to produce a record of activity called an electromyogram.

Recent advances in EMG have opened the ability to read electrical signals produced by skeletal muscles to more mainstream applications. Companies such as Thalmic Labs, Inc. of Ontario Canada have brought commercial EMG devices to market that are unobtrusive for a user to wear. These devices can connect wirelessly (via, for example, BLUETOOTH® protocols) to most modern day devices.

While traditional methods of user interaction with indicia-reading devices (such as via a trigger or touchscreen interface) are generally effective, the effectiveness of such traditional methods is not completely hands-free or touch-free.

Therefore, a need exists for more efficient and effective user interfaces for indicia-reading systems, including but not limited to indicia-reading systems that interface with a user's nervous system.

SUMMARY

Accordingly, in one aspect, the present invention embraces an indicia-reading system having an interface with a user's nervous system. The system may include a headset with electrodes capable of detecting electromagnetic signals produced in the brain of a user. The system may also include a indicia reader in communication with the headset, including a central processing unit and memory, an indicia capturing subsystem for acquiring information about indicia within the indicia-capturing subsystem's field of view, and an indicia-decoding subsystem configured for decoding indicia information acquired by the indicia-capturing subsystem. The indicia reader may be configured to monitor the electromagnetic signals detected by the headset.

In an exemplary embodiment, the indicia-reading system may include an indicia reader configured to perform an operation in response to electromagnetic signals detected by the headset.

In another exemplary embodiment, the indicia reader operation that may be performed in response to electromagnetic signals detected by the headset is acquiring information about indicia within the indicia-capturing subsystem's field of view.

In yet another exemplary embodiment, the indicia reader operation that may be performed in response to electromagnetic signals detected by the headset is placing the indicia reader into a different mode.

In yet another exemplary embodiment, the detected signals produced in the brain of the user may correspond to a facial expression.

In yet another exemplary embodiment, the detected signals produced in the brain of the user may correspond to a wink.

In yet another exemplary embodiment, the detected signals produced in the brain of the user may correspond to mental commands.

In yet another exemplary embodiment, the communication between the headset and the indicia reader may be wireless communication.

In yet another exemplary embodiment, the indicia reader may be a wearable computer.

In another aspect, the present invention may include an indicia-reading system having an interface with a user's nervous system including a band comprising electrodes capable of detecting electromagnetic signals produced in the skeletal muscles of a user. The system may also include a indicia reader in communication with the band, comprising a central processing unit and memory, an indicia capturing subsystem for acquiring information about indicia within the indicia-capturing subsystem's field of view, and an indicia-decoding subsystem configured for decoding indicia information acquired by the indicia-capturing subsystem. The indicia reader may be configured to monitor the electromagnetic signals detected by the band.

In an exemplary embodiment, the indicia reader may be configured to perform an operation in response to electromagnetic signals detected by the band.

In another exemplary embodiment, the indicia reader operation in response to electromagnetic signals detected by the band may be acquiring information about indicia within the indicia-capturing subsystem's field of view.

In yet another exemplary embodiment, the indicia reader operation in response to electromagnetic signals detected by the band may be placing the indicia reader into a different scanning mode.

In yet another exemplary embodiment, the detected signals produced in the skeletal muscles of a user may correspond to arm or hand gestures.

In yet another exemplary embodiment, the detected gesture may be a snap of two fingers.

In yet another exemplary embodiment, the detected gesture may be a clenched fist.

In yet another exemplary embodiment, the detected gesture may be a combination of hand, finger, or arm movements.

In yet another exemplary embodiment, the band may be an arm band configured to be worn on the user's forearm.

In another aspect, the present invention may include a vehicle safety system having an interface with a user's nervous system including a headset with electrodes capable of detecting electromagnetic signals produced in the brain of a user. The system may also include a vehicle computer including a central processing unit and memory in communication with the headset. The vehicle computer may be configured to monitor the electromagnetic signals detected by the headset.

In an exemplary embodiment, the vehicle computer may be configured to perform an operation in response to electromagnetic signals detected by the headset.

The foregoing illustrative summary, as well as other exemplary objectives and/or advantages of the invention, and the manner in which the same are accomplished, are further explained within the following detailed description and its accompanying drawings.

DETAILED DESCRIPTION

The present invention embraces systems that interface with a user's nervous system. In particular, the present invention embraces hands-free indicia-reading systems that interface with a user's nervous system. Although indicia-reading systems are typically referred to herein, a person having skill in the art will recognize that the systems that interact with a user's nervous system may be utilized in other environments as set forth herein (e.g., for use with vehicle safety systems).

The term indicia as used herein is intended to refer broadly to various types of machine-readable indicia, including barcodes, QR codes, matrix codes, 1D codes, 2D codes, RFID tags, characters, etc. The indicia are typically graphical representations of information (e.g., data) such as product numbers, package tracking numbers, or personnel identification numbers. The use of indicia readers to input data into a system, rather than manual data entry, results in generally faster and more reliable data entry.

An exemplary indicia-reading system according to the present invention may include an electroencephalogram in the form of a headset that a user will wear and an indicia-reading device in electronic communication with the headset. When certain brainwave activity is detected by the headset, the system is configured to trigger operations of the indicia reader.

In another exemplary embodiment, an indicia-reading system according to the present invention may include an electromyograph band that a user may wear on their arm and an indicia reading device in electronic communication with the band. When certain skeletal muscle activity is detected by the band, the system is configured trigger operations of the indicia reader.

Non-limiting examples of typical indicia-reading devices may include handheld computers, handheld scanners, wearable computers, and similar products. Preferably, a wearable computer may be used in the exemplary embodiments disclosed herein for ease of user interface. References in the disclosure to particular types of devices are not intended to limit the disclosure to particular devices.

Figure 1:
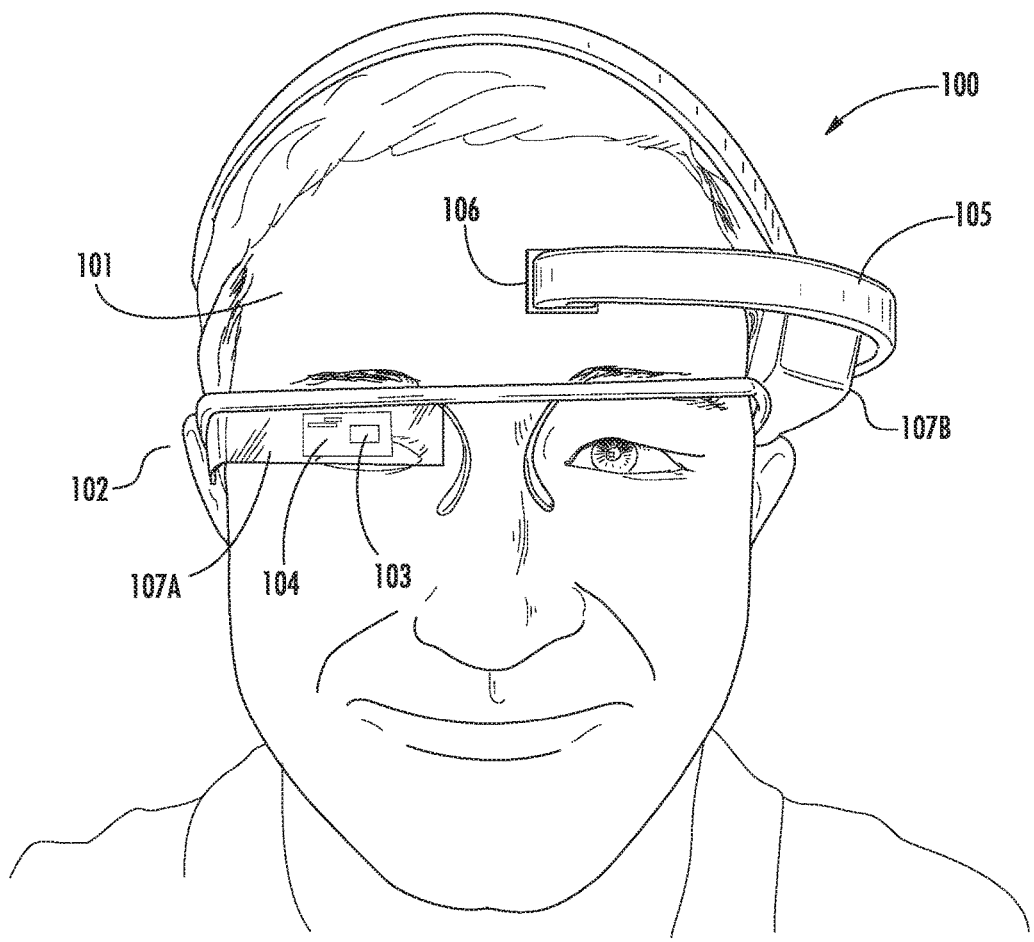
FIG. 1 graphically depicts a user wearing certain components of an exemplary indicia-reading system according to the present invention.

Referring now to the drawings, FIG. 1 depicts a user 101 wearing an exemplary indicia-reading system 100 having an interface with a user's nervous system, specifically an indicia-reading system having an interface with a user's brain.

The exemplary indicia-reading system 100 includes an indicia-reading wearable computer 102 (e.g., GOOGLE GLASS™ from Google, Inc.). Although a certain type of wearable computer 102 is depicted, various types of wearables or other kinds of devices that read indicia may alternatively be used (e.g., hand-held indicia readers such as trigger-type readers and mobile computing devices like smartphones).

Figure 3:
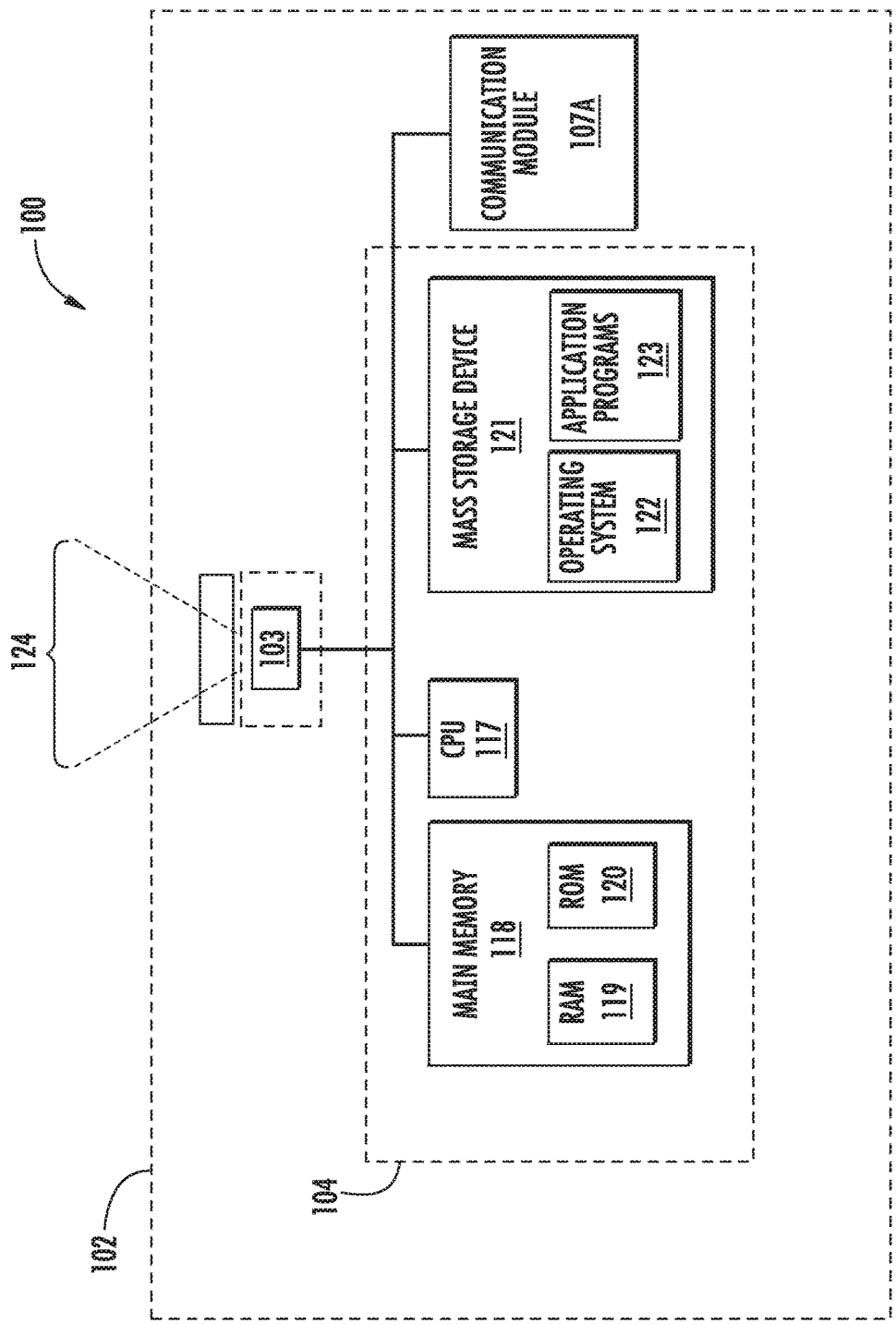
FIG. 3 is a block diagram illustrating certain components of an exemplary indicia-reading system according to the present invention.

The wearable computer 102 of the exemplary indicia-reading system 100 may include an indicia-capturing subsystem 103 (FIG. 1 and FIG. 3). In some instances, indicia-capturing subsystem 103 may include laser scanning subsystems that sweep light beams (e.g., a laser beam) across a scan path (i.e., a field of view), and then receive the optical signals that reflect or scatter off the indicium. Typically, in this type of embodiment the optical signal is received using a photoreceptor (e.g., photodiode) and is converted into an electrical signal. The electrical signal is an electronic representation of the indicia information (e.g., the data represented by the indicia). When in the form of an electrical signal, this information can be processed (e.g., decoded) by an indicia-decoding subsystem 104.

In other instances, the indicia-capturing subsystem 103 (FIG. 1 and FIG. 3) may include an imaging subsystem (e.g., the built-in camera of a smartphone, tablet, or wearable computer such as GOOGLE GLASS™) or some combination of an imaging subsystem and a laser scanning subsystem. The imaging subsystem captures digital images of objects within the subsystem's field of view 124 (FIG. 3) (e.g., 1D, 2D, and Postal barcodes).

When the indicia information takes the form of a digital image, the indicia information is typically processed by an indicia-decoding subsystem 104 (FIG. 3) through the use of image-processing software (e.g., optical character recognition (OCR) technology), which can both identify the presence of indicia in the digital image and decode the indicia. The components of indicia-decoding subsystem 104 are known in the art and may include a storage memory 118 for transmitting the signal to a central processing unit (CPU) 117 for processing digital signals. The exemplary wearable computer 102 may also include random access memory (RAM) 119, a read only memory (ROM) 120, and a mass storage device 121 (e.g., flash memory, a hard drive, etc.) with an operating system 122 and applications programs 123 (FIG. 3).

The exemplary indicia-reading system 100 also includes a EEG headset 105 (e.g., the EMOTIVE INSIGHT™ from Emotiv Systems, NEUROSKY® EEG biosensor from NeuroSky of San Jose, California, or similar devices) with a number of electrodes 106 capable of detecting signals produced in the brain of a user 101. For instance, EEG headset 105 is capable of producing a graph measurement of a user's 101 brain waves. The electrodes 106 are, for example, disks that conduct electrical activity, capture it from the brain, and convey it out through an amplifier.

As EEG technology has progressed, researchers (e.g., researchers at Emotiv Systems) have applied the technology to create high-fidelity brain computer interface systems that can read and interpret conscious and non-conscious thoughts as well as emotions. In this regard, the electrodes 106 of the exemplary indicia-reading system 100 can be used to record the resulting brain waves during a user's 101 concentration. Thereafter, the electrical activity of the user's 101 brain waves can be correlated based upon the recorded pattern to, for example, the user's 101 state of mind or, for example, to when the user 101 performs a facial expression (e.g., a wink, a smile, a frown, etc.).

A communication module pair 107A, 107B may be included respectively in the wearable computer 102 and the headset 105 of the exemplary indicia-reading system 100 for data communication. The wireless communication may include, but is not limited to, ZIGBEE® and BLUETOOTH® protocols. Although wireless communication is preferred (e.g., to provide the user with a greater range of motion), a wired connection may also be used.

Through the interface between the headset 105 and the wearable computer 102, EEG brainwave activity can be communicated in near real-time. For example, a software application program 123 running on the wearable computer 102 can monitor the user's 101 brainwave activity. The wearable computer 102 can be configured to trigger a scan event to the indicia-capturing subsystem 103 when the triggering event is detected using a software application program (such as, for example, SWIFTDECODER MOBILE™ barcode decoding software from Honeywell International, Inc.). By way of example, the relevant events to trigger a scan event to the indicia-capturing subsystem 103 may include a facial gesture such as a strong blink by the user 101, or a mental command such as when the user 101 focuses intensely on a particular location or imagines pushing a barcode away.

In addition to a trigger for a scan event to the indicia-capturing subsystem 103, mental commands or gesture commands can also be used to trigger any other operation feature in the indicia-reader 102 such as putting it into a different mode (e.g., presentation scanning), turning on and off the indicia-reader's illumination feature, or any other feature that the indicia-reader supports.

The software programs 123 can also, for example, be configured to recognize the direction a user 101 is looking in order to determine which indicia to return to the indicia-decoding subsystem 104 when multiple indicia are present in the field of view 124 (FIG. 3). The trigger command may be used to initially begin the scan event, and all indicia in the field of view 124 could then be captured by the indicia-capturing subsystem 103 and decoded by the indicia-decoding subsystem 104. If multiple indicia were present in the field of view, the indicia closest to the direction in which the user 101 was viewing can be captured by the indicia-capturing subsystem 103 and returned to the indicia-decoding subsystem 104.

Figure 2:
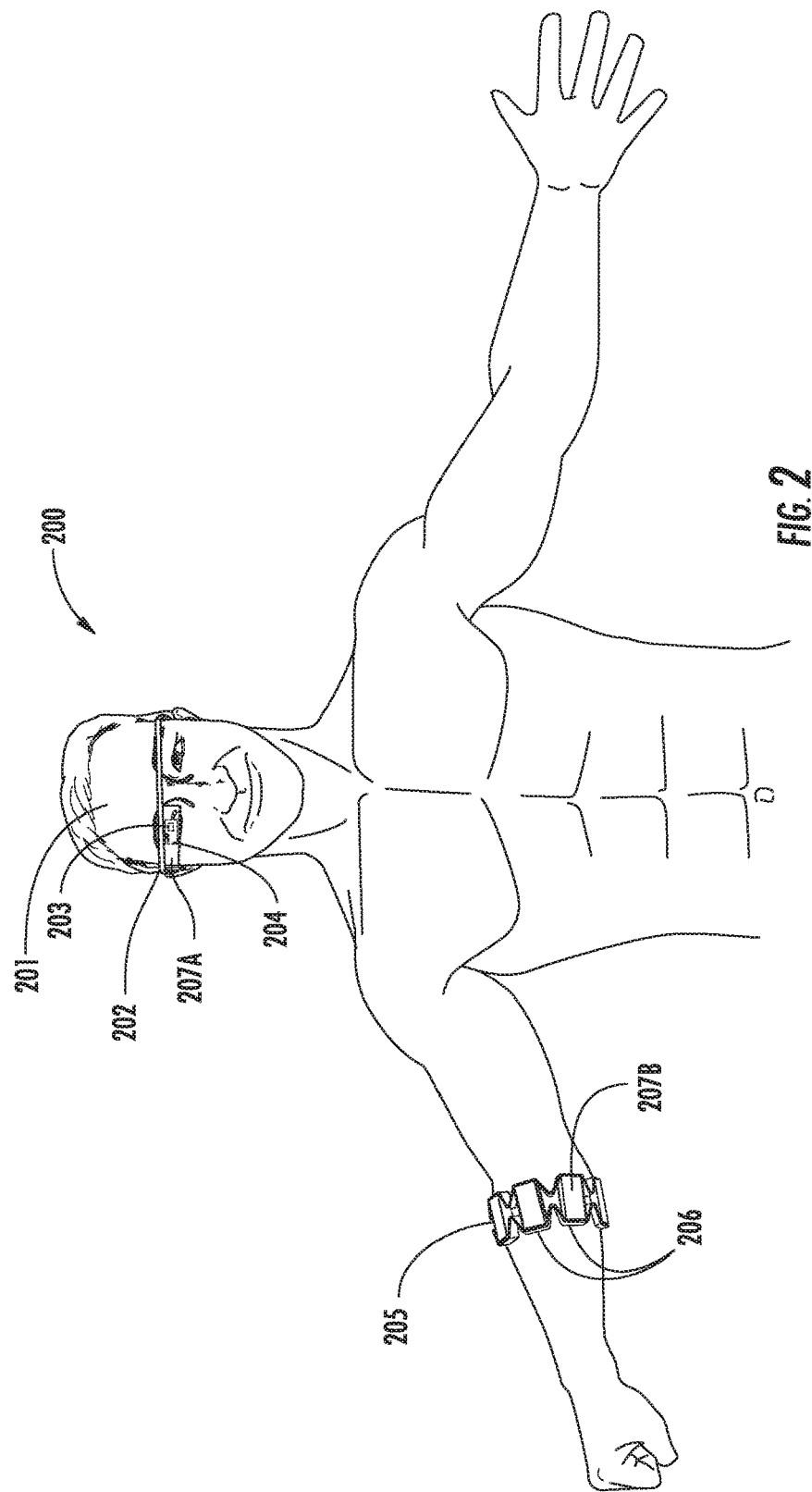
FIG. 2 graphically depicts a user wearing certain components of another exemplary indicia-reading system according to the present invention.

FIG. 2 depicts certain components of another exemplary indicia-reading system 200 according to the present invention. The components of the exemplary system 200 depicted at FIG. 2 also provide an interface with a user's nervous system, but rather than interfacing with a user's brain as with system 100, the indicia-reading system 200 interfaces with a user's skeletal muscle activity.

A person having skill in the art will recognize that the relevant discussion with regard to the interface with a user's brain described above and depicted at FIGS. 1 and 3 is applicable to the indicia-reading system 200 that interacts with a user's skeletal muscle activity. Referring to the indicia reading system 200, the system may have elements 202, 203, 204, 205, 206, 207A, and 207B, which operate in a similar manner as corresponding elements 102, 103, 104, 105, 106, 107A, and 107B of indicia-reading system 100.

The exemplary indicia-reading system 200 includes an electromyography (EMG) band 205 that a user 201 may wear on their forearm (e.g., the MYO™ EEG arm-band developed by Thalmic Labs, Inc. of Ontario Canada or related devices). Similar to the discussion regarding EEG technology above, researchers (e.g., researchers at Thalmic Labs) have applied EMG technology to read the electrical activity of a user's muscles to allow for control of a device. In this regard, the band 205 contains a number of electrodes 206 that can read the electrical activity of a user's muscles.

An indicia-reading device, for example wearable computer 202, is in electronic communication to the band 205. The communication channels may be wired or wireless, but preferably includes wireless communication using a wireless communication module 207A, 207B.

When certain skeletal muscle activity is detected by the band 205, the system 200 is configured trigger operations of an indicia reader 202 using hardware and software programs of the type described above with reference to FIGS. 1 and 3. The trigger event may be based upon the detected electrical activity of the user's muscles such as when the user 202 performs an arm or hand gesture. The trigger may include, for example, the snap of two fingers, the rotation of the arm, clench of the fist, touching of two fingers, or various other combinations of hand, finger, or arm movements.

In addition to a trigger for a scan event, muscular activity commands can also be used to trigger other operations in the indicia-reader (e.g., wearable computer 202) such as putting it into a different mode (e.g., presentation scanning), tuning and off the indicia-reader's illumination feature, or any other feature that the indicia-reader supports. The EMG band 205 could also be used to holster an arm mounted device/computer in addition to providing a gesture recognition system.

In another exemplary embodiment, systems that interface with a user's nervous system may be utilized to control or monitor vehicles such as forklifts, cranes, delivery trucks and similar industrial vehicles (e.g., vehicles used in industrial operations, factory or warehouse settings, and the like). References in the disclosure to particular types of vehicles are not intended to limit the disclosure to particular vehicles.

Figure 4:
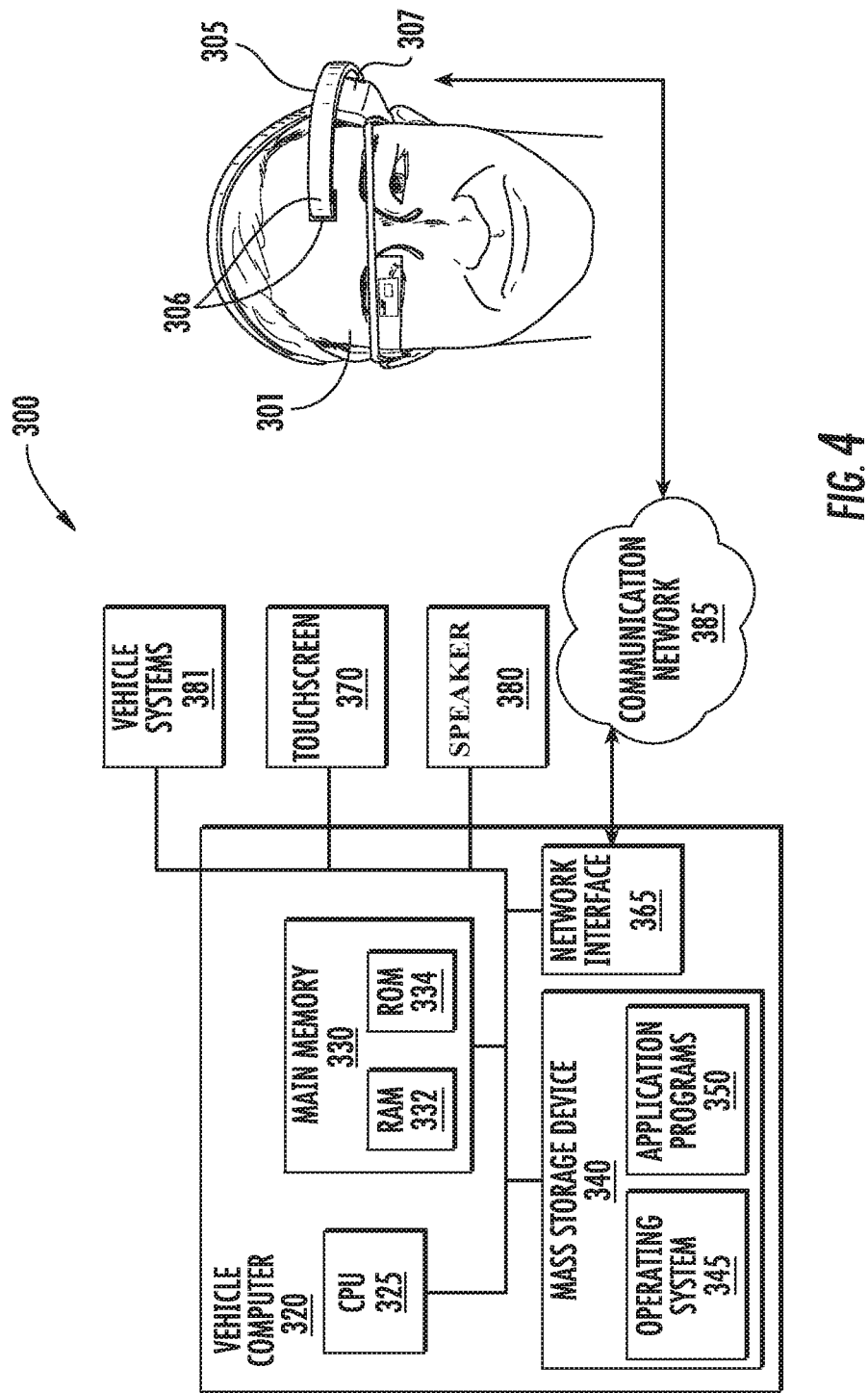
FIG. 4 is a block diagram illustrating certain components of an exemplary system that interfaces with a user's nervous system according to the present invention.

FIG. 4 is a block diagram illustrating certain components of an exemplary system 300 that interfaces with a user's nervous system and that may be utilized to control or monitor vehicles, such as forklifts, according to the present invention. The exemplary system 300 is related to detecting or preventing a safety related incident quickly before or after it has occurred.

Some vehicle safety systems may use inertial sensors, cameras, or other sensors to detect safety-related events. The exemplary system 300 utilizes a user's brain response to an incident to trigger a notification/alarm or responsive action by the vehicle. Such events may include, but are not limited to, the imminent collision of a forklift and a person, an operator that is losing focus on a particular task at hand, or a driver falling asleep at the wheel. The system 300 is related to detecting these events and their warning signs. Further, system 300 may be utilized to prevent the occurrence of safety incidents.

The exemplary system 300 includes an EEG headset 305 which may be of the type described above with regard to indicia-reading system 100. The headset 305 includes electrodes 306 that conduct electrical activity, capture it from the brain of a user 301, and convey it out through an amplifier. A communication module 307 may be included for data communication.

The system 300 may also include a vehicle computer 320 which may be mounted within the applicable vehicle. Rather than a vehicle-mounted computer, other computing devices may alternatively be used (e.g., wearable or handheld computing devices). Exemplary vehicle computer 320 includes a mass storage device 340 (e.g., a solid state drive, optical drive, removable flash drive or any other component with similar storage capabilities) for storing an operating system 345 (e.g., WINDOWS® 7 and WINDOWS® EMBEDDED COMPACT (i.e., WINDOWS® CE) from MICROSOFT® CORPORATION of Redmond, Wash., and the LINUX® open source operating system) and various application programs 350. The mass storage device 340 may store other types of information as well.

Main memory 330 provides for storage of instructions and information directly accessible by central processing unit (CPU) 325. Main memory 330 may be configured to include random-access memory 332 (RAM) and read-only memory 334 (ROM). The ROM 334 may permanently store firmware or a basic input/output system (BIOS), which provide first instructions to vehicle-mount computer 320 when it is booted. RAM 332 may serve as temporary and immediately accessible storage for operating system 345 and application programs 350.

As illustrated in FIG. 4, computer touch screen 370 may be provided for inputting and displaying information using vehicle-mount computer 320. Computer touch screen 370 is operably connected to, and in communication with, vehicle-mount computer 320. Although touch screen 370 is illustrated in FIG. 4, other input devices (e.g., keyboard or mouse) or display devices may be utilized in connection with vehicle mount computer 320. The vehicle computer 320 may also include speaker 380 or other types of internal or external sound output devices.

As depicted in FIG. 4, the vehicle-mount computer 320 of the exemplary system 300 may also include network interface 365. Network interface 365 is operably connected to communications network 385, enabling vehicle-mount computer 320 to communicate with communications network 385. Communications network 385 may include any collection of computers or communication devices interconnected by communication channels. The communication channels may be wired or wireless (e.g., using BLUETOOTH® protocols). Examples of such communication networks include, without limitation, local area networks, the Internet, and cellular networks.

The connection to the communications network 385 allows vehicle computer 320 to communicate with the headset 305. The vehicle computer 320 may also be in communication with vehicle systems 381 such as a controlled braking system (e.g., wired or wireless communication). As described above with regard to system 100, the EEG headset 305 can monitor the user's 301 EEG activity in near real time and transmit the activity to the vehicle computer 320. The EEG headset 305 allows for the monitoring of attention, focus, engagement, interest, excitement, affinity, relaxation and stress, all of which can be used to make inferences into the activity being performed by the user 301.

In one embodiment, a sudden detection of high excitement from the user 301 could be used to trigger vehicle systems 381 such as a controlled breaking system on a forklift, given that a state of high excitement could be due to someone stepping in front of the vehicle. The predictive breaking system could go into effect before the forklift operator had time to consciously process what has happened and engage in an appropriate response.

In another embodiment, a user 301 might be operating a piece of heavy machinery and start to lose focus on the task at hand. The vehicle system 381 would then either perform a controlled slow down or completely stop the machinery until the operator 301 has given the task of operation their full attention.

In another embodiment, a motor vehicle user 301 could be monitored using the headset 305 for signs of drowsiness, which would sound an alarm through speakers 380, or a vehicle system 381 (e.g., an ignition lock-out system) could prevent the user 301 from operating the vehicle until the state of alertness was improved. A person having skill in the art will recognize that system 300 could be configured for use for multiple different safety/vehicle situations, and system 301 is not limited to the exemplary configurations referenced above.

To supplement the present disclosure, this application incorporates entirely by reference the following commonly assigned patents, patent application publications, and patent applications:

U.S. Pat. Nos. 6,832,725; 7,128,266;
U.S. Pat. Nos. 7,159,783; 7,413,127;
U.S. Pat. Nos. 7,726,575; 8,294,969;
U.S. Pat. Nos. 8,317,105; 8,322,622;
U.S. Pat. Nos. 8,366,005; 8,371,507;
U.S. Pat. Nos. 8,376,233; 8,381,979;
U.S. Pat. Nos. 8,390,909; 8,408,464;
U.S. Pat. Nos. 8,408,468; 8,408,469;
U.S. Pat. Nos. 8,424,768; 8,448,863;
U.S. Pat. Nos. 8,457,013; 8,459,557;
U.S. Pat. Nos. 8,469,272; 8,474,712;
U.S. Pat. Nos. 8,479,992; 8,490,877;
U.S. Pat. Nos. 8,517,271; 8,523,076;
U.S. Pat. Nos. 8,528,818; 8,544,737;
U.S. Pat. Nos. 8,548,242; 8,548,420;
U.S. Pat. Nos. 8,550,335; 8,550,354;
U.S. Pat. Nos. 8,550,357; 8,556,174;
U.S. Pat. Nos. 8,556,176; 8,556,177;
U.S. Pat. Nos. 8,559,767; 8,599,957;
U.S. Pat. Nos. 8,561,895; 8,561,903;
U.S. Pat. Nos. 8,561,905; 8,565,107;
U.S. Pat. Nos. 8,571,307; 8,579,200;
U.S. Pat. Nos. 8,583,924; 8,584,945;
U.S. Pat. Nos. 8,587,595; 8,587,697;
U.S. Pat. Nos. 8,588,869; 8,590,789;
U.S. Pat. Nos. 8,596,539; 8,596,542;
U.S. Pat. Nos. 8,596,543; 8,599,271;
U.S. Pat. Nos. 8,599,957; 8,600,158;
U.S. Pat. Nos. 8,600,167; 8,602,309;
U.S. Pat. Nos. 8,608,053; 8,608,071;
U.S. Pat. Nos. 8,611,309; 8,615,487;
U.S. Pat. Nos. 8,616,454; 8,621,123;
U.S. Pat. Nos. 8,622,303; 8,628,013;
U.S. Pat. Nos. 8,628,015; 8,628,016;
U.S. Pat. Nos. 8,629,926; 8,630,491;
U.S. Pat. Nos. 8,635,309; 8,636,200;
U.S. Pat. Nos. 8,636,212; 8,636,215;
U.S. Pat. Nos. 8,636,224; 8,638,806;
U.S. Pat. Nos. 8,640,958; 8,640,960;
U.S. Pat. Nos. 8,643,717; 8,646,692;
U.S. Pat. Nos. 8,646,694; 8,657,200;
U.S. Pat. Nos. 8,659,397; 8,668,149;
U.S. Pat. Nos. 8,678,285; 8,678,286;
U.S. Pat. Nos. 8,682,077; 8,687,282;
U.S. Pat. Nos. 8,692,927; 8,695,880;
U.S. Pat. Nos. 8,698,949; 8,717,494;
U.S. Pat. Nos. 8,717,494; 8,720,783;
U.S. Pat. Nos. 8,723,804; 8,723,904;
U.S. Pat. Nos. 8,727,223; D702,237;
U.S. Pat. Nos. 8,740,082; 8,740,085;
U.S. Pat. Nos. 8,746,563; 8,750,445;
U.S. Pat. Nos. 8,752,766; 8,756,059;
U.S. Pat. Nos. 8,757,495; 8,760,563;
U.S. Pat. Nos. 8,763,909; 8,777,108;
U.S. Pat. Nos. 8,777,109; 8,779,898;
U.S. Pat. Nos. 8,781,520; 8,783,573;
U.S. Pat. Nos. 8,789,757; 8,789,758;
U.S. Pat. Nos. 8,789,759; 8,794,520;
U.S. Pat. Nos. 8,794,522; 8,794,526;
U.S. Pat. Nos. 8,798,367; 8,807,431;
U.S. Pat. Nos. 8,807,432; 8,820,630;
International Publication No. 2013/163789;
International Publication No. 2013/173985;
International Publication No. 2014/019130;
International Publication No. 2014/110495;
U.S. Patent Application Publication No. 2008/0185432;
U.S. Patent Application Publication No. 2009/0134221;
U.S. Patent Application Publication No. 2010/0177080;
U.S. Patent Application Publication No. 2010/0177076;
U.S. Patent Application Publication No. 2010/0177707;
U.S. Patent Application Publication No. 2010/0177749;
U.S. Patent Application Publication No. 2011/0202554;
U.S. Patent Application Publication No. 2012/0111946;
U.S. Patent Application Publication No. 2012/0138685;
U.S. Patent Application Publication No. 2012/0168511;
U.S. Patent Application Publication No. 2012/0168512;
U.S. Patent Application Publication No. 2012/0193423;
U.S. Patent Application Publication No. 2012/0203647;
U.S. Patent Application Publication No. 2012/0223141;
U.S. Patent Application Publication No. 2012/0228382;
U.S. Patent Application Publication No. 2012/0248188;
U.S. Patent Application Publication No. 2013/0043312;
U.S. Patent Application Publication No. 2013/0056285;
U.S. Patent Application Publication No. 2013/0070322;
U.S. Patent Application Publication No. 2013/0075168;
U.S. Patent Application Publication No. 2013/0082104;
U.S. Patent Application Publication No. 2013/0175341;
U.S. Patent Application Publication No. 2013/0175343;
U.S. Patent Application Publication No. 2013/0200158;
U.S. Patent Application Publication No. 2013/0256418;
U.S. Patent Application Publication No. 2013/0257744;
U.S. Patent Application Publication No. 2013/0257759;
U.S. Patent Application Publication No. 2013/0270346;
U.S. Patent Application Publication No. 2013/0278425;
U.S. Patent Application Publication No. 2013/0287258;
U.S. Patent Application Publication No. 2013/0292475;
U.S. Patent Application Publication No. 2013/0292477;
U.S. Patent Application Publication No. 2013/0293539;
U.S. Patent Application Publication No. 2013/0293540;
U.S. Patent Application Publication No. 2013/0306728;
U.S. Patent Application Publication No. 2013/0306730;
U.S. Patent Application Publication No. 2013/0306731;
U.S. Patent Application Publication No. 2013/0307964;
U.S. Patent Application Publication No. 2013/0308625;
U.S. Patent Application Publication No. 2013/0313324;
U.S. Patent Application Publication No. 2013/0313325;
U.S. Patent Application Publication No. 2013/0341399;
U.S. Patent Application Publication No. 2013/0342717;
U.S. Patent Application Publication No. 2014/0001267;
U.S. Patent Application Publication No. 2014/0002828;
U.S. Patent Application Publication No. 2014/0008430;
U.S. Patent Application Publication No. 2014/0008439;
U.S. Patent Application Publication No. 2014/0025584;
U.S. Patent Application Publication No. 2014/0027518;
U.S. Patent Application Publication No. 2014/0034734;
U.S. Patent Application Publication No. 2014/0036848;
U.S. Patent Application Publication No. 2014/0039693;
U.S. Patent Application Publication No. 2014/0042814;
U.S. Patent Application Publication No. 2014/0049120;
U.S. Patent Application Publication No. 2014/0049635;
U.S. Patent Application Publication No. 2014/0061305;
U.S. Patent Application Publication No. 2014/0061306;
U.S. Patent Application Publication No. 2014/0063289;
U.S. Patent Application Publication No. 2014/0066136;
U.S. Patent Application Publication No. 2014/0067692;
U.S. Patent Application Publication No. 2014/0070005;
U.S. Patent Application Publication No. 2014/0071840;
U.S. Patent Application Publication No. 2014/0074746;
U.S. Patent Application Publication No. 2014/0075846;
U.S. Patent Application Publication No. 2014/0076974;
U.S. Patent Application Publication No. 2014/0078341;
U.S. Patent Application Publication No. 2014/0078342;
U.S. Patent Application Publication No. 2014/0078345;
U.S. Patent Application Publication No. 2014/0084068;

U.S. Patent Application Publication No. 2014/0097249;
U.S. Patent Application Publication No. 2014/0098792;
U.S. Patent Application Publication No. 2014/0100774;
U.S. Patent Application Publication No. 2014/0100813;
U.S. Patent Application Publication No. 2014/0103115;
U.S. Patent Application Publication No. 2014/0104413;
U.S. Patent Application Publication No. 2014/0104414;
U.S. Patent Application Publication No. 2014/0104416;
U.S. Patent Application Publication No. 2014/0104451;
U.S. Patent Application Publication No. 2014/0106594;
U.S. Patent Application Publication No. 2014/0106725;
U.S. Patent Application Publication No. 2014/0108010;
U.S. Patent Application Publication No. 2014/0108402;
U.S. Patent Application Publication No. 2014/0108682;
U.S. Patent Application Publication No. 2014/0110485;
U.S. Patent Application Publication No. 2014/0114530;
U.S. Patent Application Publication No. 2014/0124577;
U.S. Patent Application Publication No. 2014/0124579;
U.S. Patent Application Publication No. 2014/0125842;
U.S. Patent Application Publication No. 2014/0125853;
U.S. Patent Application Publication No. 2014/0125999;
U.S. Patent Application Publication No. 2014/0129378;
U.S. Patent Application Publication No. 2014/0131438;
U.S. Patent Application Publication No. 2014/0131441;
U.S. Patent Application Publication No. 2014/0131443;
U.S. Patent Application Publication No. 2014/0131444;
U.S. Patent Application Publication No. 2014/0131445;
U.S. Patent Application Publication No. 2014/0131448;
U.S. Patent Application Publication No. 2014/0133379;
U.S. Patent Application Publication No. 2014/0136208;
U.S. Patent Application Publication No. 2014/0140585;
U.S. Patent Application Publication No. 2014/0151453;
U.S. Patent Application Publication No. 2014/0152882;
U.S. Patent Application Publication No. 2014/0158770;
U.S. Patent Application Publication No. 2014/0159869;
U.S. Patent Application Publication No. 2014/0160329;
U.S. Patent Application Publication No. 2014/0166755;
U.S. Patent Application Publication No. 2014/0166757;
U.S. Patent Application Publication No. 2014/0166759;
U.S. Patent Application Publication No. 2014/0166760;
U.S. Patent Application Publication No. 2014/0166761;
U.S. Patent Application Publication No. 2014/0168787;
U.S. Patent Application Publication No. 2014/0175165;
U.S. Patent Application Publication No. 2014/0175169;
U.S. Patent Application Publication No. 2014/0175172;
U.S. Patent Application Publication No. 2014/0175174;
U.S. Patent Application Publication No. 2014/0191644;
U.S. Patent Application Publication No. 2014/0191913;
U.S. Patent Application Publication No. 2014/0197238;
U.S. Patent Application Publication No. 2014/0197239;
U.S. Patent Application Publication No. 2014/0197304;
U.S. Patent Application Publication No. 2014/0203087;
U.S. Patent Application Publication No. 2014/0204268;
U.S. Patent Application Publication No. 2014/0214631;
U.S. Patent Application Publication No. 2014/0217166;
U.S. Patent Application Publication No. 2014/0217180;
U.S. patent application Ser. No. 13/367,978 for a Laser Scanning Module Employing an Elastomeric U-Hinge Based Laser Scanning Assembly, filed Feb. 7, 2012 (Feng et al.);
U.S. patent application Ser. No. 29/436,337 for an Electronic Device, filed Nov. 5, 2012 (Fitch et al.);
U.S. patent application Ser. No. 13/771,508 for an Optical Redirection Adapter, filed Feb. 20, 2013 (Anderson);
U.S. patent application Ser. No. 13/852,097 for a System and Method for Capturing and Preserving Vehicle Event Data, filed Mar. 28, 2013 (Barker et al.);
U.S. patent application Ser. No. 13/902,110 for a System and Method for Display of Information Using a Vehicle-Mount Computer, filed May 24, 2013 (Hollifield);
U.S. patent application Ser. No. 13/902,144, for a System and Method for Display of Information Using a Vehicle-Mount Computer, filed May 24, 2013 (Chamberlin);
U.S. patent application Ser. No. 13/902,242 for a System For Providing A Continuous Communication Link With A Symbol Reading Device, filed May 24, 2013 (Smith et al.);
U.S. patent application Ser. No. 13/912,262 for a Method of Error Correction for 3D Imaging Device, filed Jun. 7, 2013 (Jovanovski et al.);
U.S. patent application Ser. No. 13/912,702 for a System and Method for Reading Code Symbols at Long Range Using Source Power Control, filed Jun. 7, 2013 (Xian et al.);
U.S. patent application Ser. No. 29/458,405 for an Electronic Device, filed Jun. 19, 2013 (Fitch et al.);
U.S. patent application Ser. No. 13/922,339 for a System and Method for Reading Code Symbols Using a Variable Field of View, filed Jun. 20, 2013 (Xian et al.);
U.S. patent application Ser. No. 13/927,398 for a Code Symbol Reading System Having Adaptive Autofocus, filed Jun. 26, 2013 (Todeschini);
U.S. patent application Ser. No. 13/930,913 for a Mobile Device Having an Improved User Interface for Reading Code Symbols, filed Jun. 28, 2013 (Gelay et al.);
U.S. patent application Ser. No. 29/459,620 for an Electronic Device Enclosure, filed Jul. 2, 2013 (London et al.);
U.S. patent application Ser. No. 29/459,681 for an Electronic Device Enclosure, filed Jul. 2, 2013 (Chaney et al.);
U.S. patent application Ser. No. 13/933,415 for an Electronic Device Case, filed Jul. 2, 2013 (London et al.);
U.S. patent application Ser. No. 29/459,785 for a Scanner and Charging Base, filed Jul. 3, 2013 (Fitch et al.);
U.S. patent application Ser. No. 29/459,823 for a Scanner, filed Jul. 3, 2013 (Zhou et al.);
U.S. patent application Ser. No. 13/947,296 for a System and Method for Selectively Reading Code Symbols, filed Jul. 22, 2013 (Rueblinger et al.);
U.S. patent application Ser. No. 13/950,544 for a Code Symbol Reading System Having Adjustable Object Detection, filed Jul. 25, 2013 (Jiang);
U.S. patent application Ser. No. 13/961,408 for a Method for Manufacturing Laser Scanners, filed Aug. 7, 2013 (Saber et al.);
U.S. patent application Ser. No. 14/018,729 for a Method for Operating a Laser Scanner, filed Sep. 5, 2013 (Feng et al.);
U.S. patent application Ser. No. 14/019,616 for a Device Having Light Source to Reduce Surface Pathogens, filed Sep. 6, 2013 (Todeschini);
U.S. patent application Ser. No. 14/023,762 for a Handheld Indicia Reader Having Locking Endcap, filed Sep. 11, 2013 (Gannon);
U.S. patent application Ser. No. 14/035,474 for Augmented-Reality Signature Capture, filed Sep. 24, 2013 (Todeschini);
U.S. patent application Ser. No. 29/468,118 for an Electronic Device Case, filed Sep. 26, 2013 (Oberpriller et al.);
U.S. patent application Ser. No. 14/055,234 for Dimensioning System, filed Oct. 16, 2013 (Fletcher);
U.S. patent application Ser. No. 14/053,314 for Indicia Reader, filed Oct. 14, 2013 (Huck);
U.S. patent application Ser. No. 14/065,768 for Hybrid System and Method for Reading Indicia, filed Oct. 29, 2013 (Meier et al.);

U.S. patent application Ser. No. 14/074,746 for Self-Checkout Shopping System, filed Nov. 8, 2013 (Hejl et al.);

U.S. patent application Ser. No. 14/074,787 for Method and System for Configuring Mobile Devices via NFC Technology, filed Nov. 8, 2013 (Smith et al.);

U.S. patent application Ser. No. 14/087,190 for Optimal Range Indicators for Bar Code Validation, filed Nov. 22, 2013 (Hejl);

U.S. patent application Ser. No. 14/094,087 for Method and System for Communicating Information in an Digital Signal, filed Dec. 2, 2013 (Peake et al.);

U.S. patent application Ser. No. 14/101,965 for High Dynamic-Range Indicia Reading System, filed Dec. 10, 2013 (Xian);

U.S. patent application Ser. No. 14/150,393 for Indicia-reader Having Unitary Construction Scanner, filed Jan. 8, 2014 (Colavito et al.);

U.S. patent application Ser. No. 14/154,207 for Laser Barcode Scanner, filed Jan. 14, 2014 (Hou et al.);

U.S. patent application Ser. No. 14/165,980 for System and Method for Measuring Irregular Objects with a Single Camera filed Jan. 28, 2014 (Li et al.);

U.S. patent application Ser. No. 14/166,103 for Indicia Reading Terminal Including Optical Filter filed Jan. 28, 2014 (Lu et al.);

U.S. patent application Ser. No. 14/200,405 for Indicia Reader for Size-Limited Applications filed Mar. 7, 2014 (Feng et al.);

U.S. patent application Ser. No. 14/231,898 for Hand-Mounted Indicia-Reading Device with Finger Motion Triggering filed Apr. 1, 2014 (Van Horn et al.);

U.S. patent application Ser. No. 14/250,923 for Reading Apparatus Having Partial Frame Operating Mode filed Apr. 11, 2014, (Deng et al.);

U.S. patent application Ser. No. 14/257,174 for Imaging Terminal Having Data Compression filed Apr. 21, 2014, (Barber et al.);

U.S. patent application Ser. No. 14/257,364 for Docking System and Method Using Near Field Communication filed Apr. 21, 2014 (Showering);

U.S. patent application Ser. No. 14/264,173 for Autofocus Lens System for Indicia Readers filed Apr. 29, 2014 (Ackley et al.);

U.S. patent application Ser. No. 14/274,858 for Mobile Printer with Optional Battery Accessory filed May 12, 2014 (Marty et al.);

U.S. patent application Ser. No. 14/277,337 for MULTIPURPOSE OPTICAL READER, filed May 14, 2014 (Jovanovski et al.);

U.S. patent application Ser. No. 14/283,282 for TERMINAL HAVING ILLUMINATION AND FOCUS CONTROL filed May 21, 2014 (Liu et al.);

U.S. patent application Ser. No. 14/300,276 for METHOD AND SYSTEM FOR CONSIDERING INFORMATION ABOUT AN EXPECTED RESPONSE WHEN PERFORMING SPEECH RECOGNITION, filed Jun. 10, 2014 (Braho et al.);

U.S. patent application Ser. No. 14/305,153 for INDICIA READING SYSTEM EMPLOYING DIGITAL GAIN CONTROL filed Jun. 16, 2014 (Xian et al.);

U.S. patent application Ser. No. 14/310,226 for AUTOFOCUSING OPTICAL IMAGING DEVICE filed Jun. 20, 2014 (Koziol et al.);

U.S. patent application Ser. No. 14/327,722 for CUSTOMER FACING IMAGING SYSTEMS AND METHODS FOR OBTAINING IMAGES filed Jul. 10, 2014 (Oberpriller et al,);

U.S. patent application Ser. No. 14/327,827 for a MOBILE-PHONE ADAPTER FOR ELECTRONIC TRANSACTIONS, filed Jul. 10, 2014 (Hejl);

U.S. patent application Ser. No. 14/329,303 for CELL PHONE READING MODE USING IMAGE TIMER filed Jul. 11, 2014 (Coyle);

U.S. patent application Ser. No. 14/333,588 for SYMBOL READING SYSTEM WITH INTEGRATED SCALE BASE filed Jul. 17, 2014 (Barten);

U.S. patent application Ser. No. 14/334,934 for a SYSTEM AND METHOD FOR INDICIA VERIFICATION, filed Jul. 18, 2014 (Hejl);

U.S. patent application Ser. No. 14/336,188 for METHOD OF AND SYSTEM FOR DETECTING OBJECT WEIGHING INTERFERENCES, Filed Jul. 21, 2014 (Amundsen et al.);

U.S. patent application Ser. No. 14/339,708 for LASER SCANNING CODE SYMBOL READING SYSTEM, filed Jul. 24, 2014 (Xian et al.);

U.S. patent application Ser. No. 14/340,627 for an AXIALLY REINFORCED FLEXIBLE SCAN ELEMENT, filed Jul. 25, 2014 (Rueblinger et al.);

U.S. patent application Ser. No. 14/340,716 for an OPTICAL IMAGER AND METHOD FOR CORRELATING A MEDICATION PACKAGE WITH A PATIENT, filed Jul. 25, 2014 (Ellis);

U.S. patent application Ser. No. 14/342,544 for Imaging Based Barcode Scanner Engine with Multiple Elements Supported on a Common Printed Circuit Board filed Mar. 4, 2014 (Liu et al.);

U.S. patent application Ser. No. 14/345,735 for Optical Indicia Reading Terminal with Combined Illumination filed Mar. 19, 2014 (Ouyang);

U.S. patent application Ser. No. 14/336,188 for METHOD OF AND SYSTEM FOR DETECTING OBJECT WEIGHING INTERFERENCES, Filed Jul. 21, 2014 (Amundsen et al.);

U.S. patent application Ser. No. 14/355,613 for Optical Indicia Reading Terminal with Color Image Sensor filed May 1, 2014 (Lu et al.);

U.S. patent application Ser. No. 14/370,237 for WEB-BASED SCAN-TASK ENABLED SYSTEM AND METHOD OF AND APPARATUS FOR DEVELOPING AND DEPLOYING THE SAME ON A CLIENT-SERVER NETWORK filed Jul. 2, 2014 (Chen et al.);

U.S. patent application Ser. No. 14/370,267 for INDUSTRIAL DESIGN FOR CONSUMER DEVICE BASED SCANNING AND MOBILITY, filed Jul. 2, 2014 (Ma et al.);

U.S. patent application Ser. No. 14/376,472, for an ENCODED INFORMATION READING TERMINAL INCLUDING HTTP SERVER, filed Aug. 4, 2014 (Lu);

U.S. patent application Ser. No. 14/379,057 for METHOD OF USING CAMERA SENSOR INTERFACE TO TRANSFER MULTIPLE CHANNELS OF SCAN DATA USING AN IMAGE FORMAT filed Aug. 15, 2014 (Wang et al.);

U.S. patent application Ser. No. 14/452,697 for INTERACTIVE INDICIA READER, filed Aug. 6, 2014 (Todeschini);

U.S. patent application Ser. No. 14/453,019 for DIMENSIONING SYSTEM WITH GUIDED ALIGNMENT, filed Aug. 6, 2014 (Li et al.);

U.S. patent application Ser. No. 14/460,387 for APPARATUS FOR DISPLAYING BAR CODES FROM LIGHT EMITTING DISPLAY SURFACES filed Aug. 15, 2014 (Van Horn et al.);

U.S. patent application Ser. No. 14/460,829 for ENCODED INFORMATION READING TERMINAL WITH WIRELESS PATH SELECTON CAPABILITY, filed Aug. 15, 2014 (Wang et al.);

U.S. patent application Ser. No. 14/462,801 for MOBILE COMPUTING DEVICE WITH DATA COGNITION SOFTWARE, filed on Aug. 19, 2014 (Todeschini et al.);

U.S. patent application Ser. No. 14/446,387 for INDICIA READING TERMINAL PROCESSING PLURALITY OF FRAMES OF IMAGE DATA RESPONSIVELY TO TRIGGER SIGNAL ACTIVATION filed Jul. 30, 2014 (Wang et al.);

U.S. patent application Ser. No. 14/446,391 for MULTIFUNCTION POINT OF SALE APPARATUS WITH OPTICAL SIGNATURE CAPTURE filed Jul. 30, 2014 (Good et al.);

U.S. patent application Ser. No. 29/486,759 for an Imaging Terminal, filed Apr. 2, 2014 (Oberpriller et al.);

U.S. patent application Ser. No. 29/492,903 for an INDICIA SCANNER, filed Jun. 4, 2014 (Zhou et al.); and U.S. patent application Ser. No. 29/494,725 for an IN-COUNTER BARCODE SCANNER, filed Jun. 24, 2014 (Oberpriller et al.).

In the specification and/or figures, typical embodiments and environments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. An indicia-reading system having an interface with a user's nervous system, comprising:
   a band comprising electrodes capable of detecting electrical signals produced in the skeletal muscles of a user when the user makes one or more facial gestures; and
   a hands-free indicia reader in communication with the band, comprising (i) a central processing unit and memory (ii) an indicia capturing subsystem for acquiring information about indicia within the indicia-capturing subsystem's field of view, and (iii) an indicia-decoding subsystem configured for decoding indicia information acquired by the indicia-capturing subsystem;
   wherein the hands-free indicia reader is configured to monitor the electrical signals detected by the band and to perform a scanning operation in response to an electrical signal detected by the band.

2. The system according to claim 1, wherein the scanning operation comprises acquiring information about indicia within the indicia-capturing subsystem's field of view.

3. The system according to claim 1, wherein the scanning operation comprises placing the indicia reader into a different scanning mode, the different scanning mode comprising activating or deactivating a feature supported by the indicia reader.

4. The system according to claim 1, wherein the facial gesture comprises a blink or a wink by the user.

5. The system according to claim 1, wherein the facial gesture comprises the user focusing intensely on a particular location.

6. The system according to claim 5, wherein the particular location comprises a barcode.

7. The system according to claim 1, wherein the facial gesture comprises looking in a particular direction.

8. The system according to claim 1, wherein the system is configured to recognize, based at least in part on the electrical signals, a direction in which the user is looking.

9. The system according to claim 8, wherein the system is configured to identify an indicia from among a plurality of indicia present in the field of view based at least in part on the direction in which the user is looking, and to cause the indicia reader to perform a scanning operation in respect of the identified indicia.

10. An indicia-reading system having an interface with a user's nervous system, comprising:
    a band comprising electrodes capable of detecting electrical signals produced in the skeletal muscles of a user when the user makes one or more facial gestures; and
    a hands-free indicia reader in communication with the band, comprising (i) a central processing unit and memory (ii) an imaging module for capturing images of indicia within the imaging module's field of view, and (iii) an indicia-decoding subsystem configured for decoding indicia within images captured by the imaging module;
    wherein the system is configured to monitor the electrical signals detected by the band and to detect a triggering event; and
    in response to detecting the triggering event, to cause the imaging module to capture an image and cause the indicia-decoding subsystem to attempt to locate and decode an indicia in the captured image.

11. The system according to claim 10, wherein the indicia reader is configured to perform an operation in response to electrical signals detected by the band.

12. The system according to claim 11, wherein the indicia reader operation is capturing images of indicia within the imaging module's field of view.

13. The system according to claim 11, wherein the indicia reader operation is placing the indicia reader into a different scanning mode, the different scanning mode comprising activating or deactivating a feature supported by the indicia reader.

14. The system according to claim 10, wherein the facial gesture comprises a blink or a wink by the user.

15. The system according to claim 10, wherein the facial gesture comprises looking in a particular direction.

16. The system according to claim 10, wherein the system is configured to recognize, based at least in part on the electrical signals, a direction in which the user is looking.

17. The system according to claim 10, wherein the facial gesture comprises the user focusing intensely on a particular location.

18. The system according to claim 17, wherein the particular location comprises a barcode.

19. The system according to claim 18, wherein the system is configured to identify an indicia from among a plurality of indicia present in the field of view based at least in part on the direction in which the user is looking, and to cause the indicia reader to perform a scanning operation in respect of the identified indicia.

* * * * *